(12) United States Patent
Araujo et al.

(10) Patent No.: US 9,481,637 B2
(45) Date of Patent: Nov. 1, 2016

(54) COMPOUNDS FOR THE TREATMENT OF SEIZURES AND OTHER CENTRAL NERVOUS SYSTEMS DISORDERS AND CONDITIONS

(71) Applicant: Ketogen Inc., Toronto (CA)

(72) Inventors: Joseph A. Araujo, Toronto (CA); John S. Andrews, Mississauga (CA); Subhash C. Annedi, Mississauga (CA); Guy A. Higgins, Toronto (CA); Norton W. Milgram, Toronto (CA); Paula J. Estey, Neebing (CA); Gary L. W. G. Robinson, Framingham, MA (US); Jaipal R. Nagireddy, Brantford (CA)

(73) Assignee: Ketogen Inc., Toronto, Ontario (CA)

( * ) Notice: Subject to any disclaimer, the term of this patent is extended or adjusted under 35 U.S.C. 154(b) by 0 days.

(21) Appl. No.: 14/727,979

(22) Filed: Jun. 2, 2015

(65) Prior Publication Data

US 2015/0344413 A1    Dec. 3, 2015

Related U.S. Application Data

(60) Provisional application No. 62/006,515, filed on Jun. 2, 2014.

(51) Int. Cl.
| | | |
|---|---|---|
| *C07D 207/27* | (2006.01) | |
| *A61K 31/4015* | (2006.01) | |
| *C07C 233/47* | (2006.01) | |

(52) U.S. Cl.
CPC .......... *C07C 233/47* (2013.01); *A61K 31/4015* (2013.01); *C07D 207/27* (2013.01); *C07C 2101/14* (2013.01)

(58) Field of Classification Search
CPC .................. C07D 207/27; A61K 31/4015
See application file for complete search history.

(56) References Cited

FOREIGN PATENT DOCUMENTS

| | | |
|---|---|---|
| CA | 2577490 A1 | 3/2006 |
| CA | 2740087 A1 | 4/2010 |
| CA | 2783016 A1 | 11/2013 |
| ES | 2326355 A1 | 10/2009 |

OTHER PUBLICATIONS

Chang, Pishan, et al., "Seizure control by ketogenic diet-associated medium chain fatty acids", Neuropharmacology, 69, 2013, 105-114.
Zarnowska, Iwona, et al., "Pharmacodynamic and pharmacokinetic interactions between common antiepileptic drugs and acetone, the chief anticonvulsant ketone body elevated in the ketogenic diet in mice", Epilepsia, 50 (5):1132-1140, 2009.
Loscher, Wolfgang, et al., "New avenues for anti-epileptic drug discovery and development", Nature Reviews, vol. 12, Oct. 2013, 757-776.
International Search Report and Written Opinion of corresponding PCT/CA2015/050507 dated Aug. 26, 2015.

*Primary Examiner* — Robert Havlin
(74) *Attorney, Agent, or Firm* — Bereskin & Parr LLP/S.E.N.C.R.L., s.r.l.; Patricia Folkins

(57) ABSTRACT

The present application relates to novel compounds comprising a moiety that leads to the metabolic production of ketones bonded to a ketone-potentiated anti-epileptic drug, compositions comprising these compounds, and their use, for example for the treatment of epilepsy, and other CNS diseases, disorders or conditions. In particular, the present application includes compounds of Formula I, and compositions and uses thereof:

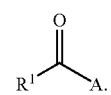

17 Claims, 16 Drawing Sheets

COMPOUNDS FOR THE TREATMENT OF SEIZURES AND OTHER CENTRAL NERVOUS SYSTEMS DISORDERS AND CONDITIONS

CROSS-REFERENCE TO RELATED APPLICATIONS

The present application claims the benefit of priority from U.S. provisional application No. 62/006,515 filed on Jun. 2, 2014, the contents of which are incorporated herein by reference in their entirety.

FIELD

The present application relates to novel compounds comprising a moiety that leads to the metabolic production of ketones bonded to a ketone-potentiated anti-epileptic drug, compositions comprising these compounds, and their use, for example for the treatment of epilepsy, seizures, and/or other central nervous system disorders or conditions.

BACKGROUND

Epilepsy is a neurological condition that makes people prone to seizures. A seizure is a change in sensation, awareness, or behavior brought about by a brief electrical disturbance in the brain. Seizures vary from a momentary disruption of the senses, to short periods of unconsciousness or staring spells, to convulsions (Fisher et al., *Epilepsia* 46: 470-472, 2005). Some people have just one type of seizure. Others have more than one type. All seizures are caused by the same thing: a sudden change in how the cells of the brain send electrical signals to each other.

During epilepsy, a propagation of high frequency, continuous firing is initiated, referred to as a seizure. The severity and symptoms of this seizure will depend on the position of the initial focal point, seizure length, frequency of the discharges and the distance the propagation spreads. Essentially, what a patient experiences during a seizure will depend on where in the brain the epileptic activity begins and how widely and rapidly it spreads. Neurons may fire up to 500 times a second during an epileptic seizure, over six times the normal rate of about 80 times a second. The onset of epilepsy is defined as a condition characterized by recurrent, unprovoked seizures.

There are over 40 different types of seizures, ranging from seizures that go totally unnoticed by others to tonic-clonic seizures which involve muscular contraction, uncontrollable jerks and loss of consciousness. Knowing which type of seizures a person has is useful as this will determine which antiepileptic drug (AED) is most likely to be of benefit. However, the choice of the AED also depends on several other issues, including the age and sex of the patient, requirements for compliance and the presence of hard-to-treat epileptic syndromes. The causes of epilepsy can be divided into three categories:

Symptomatic epilepsy has a known cause, e.g. structural abnormality of the brain, including head trauma, birth trauma, cerebrovascular disorders, cerebral anoxia and brain tumors. Idiopathic epilepsy has no clear underlying cause for the sudden start of the seizures, although it is thought that having a low seizure threshold could be a contributing factor. Cryptogenic epilepsy may be symptomatic or idiopathic. This form of epilepsy is believed to be symptomatic of a hidden cause of unknown etiology, although unlike idiopathic epilepsy, it is not thought to have started due to a low seizure threshold.

Epilepsy is the one of the most common neurological disorders with approximately 3.3 Million patients in North America and almost 200,000 new cases annually (Banerjee et al., *Epilepsy Res.* 85: 31-45, 2009 and *Epilepsy Prevalence, Incidence and Other Statistics* (2011).

Since the introduction of barbiturates as the first anticonvulsant therapy there have been many drugs discovered and developed to treat the disorder. However, despite the many therapeutic options available, a large number of patients are refractory to antiepileptic treatments: patients either fail to respond to any drug treatment or have a poor response with continuing seizures.

Currently, treatment of epilepsy is symptom-focused, i.e., to reduce or eliminate seizure response. While many new AEDs have been commercialized in the past 15 years with improved seizure control and reduced side effects, there still remain important unmet medical needs in the treatment of epilepsy. Successful management of epilepsy still remains a significant problem as demonstrated by the fact that despite using various combinations of AEDs, 20-25% of epileptic patients are insensitive to currently available medication. Therefore, there is an ongoing need to discover and develop effective drugs or synergistic combinations of drugs for treating epilepsy.

Following observations that fasting can decrease the incidence of seizures in epilepsy patients, it was hypothesised that this was due to the production of ketones as metabolism switched from carbohydrates to lipids. Although glucose metabolism is the primary source of brain energy, ketone metabolism provides an alternative pathway, which normally occurs under starvation conditions. Ketone bodies are a natural endogenous energy source mainly produced by the liver from mobilisation of endogenous body fat and utilised by extrahepatic tissues (brain, heart, kidney, muscle, etc.).

The ketogenic diet was introduced in the 1920's as a high fat diet which would produce elevated levels of ketone bodies in the plasma (Maalouf et al., *Brain Res Rev.* 59: 293-315, 2009 and Hartman et al., *Pediatr Neurol.* 36: 281-292, 2007). The diet proved to be effective in many patients who failed to respond to conventional treatment and has remained a mainstay or adjunctive treatment for drug resistant patients. Investigations indicated that the diet was an effective anti-seizure treatment in animals (Hartman et al., *Pediatric Neurol.* 36: 281-292, 2007) as well as humans. The diet is, however, unpalatable and failure to adhere to the diet leads to a return or increase in seizures. In addition, the health consequences of a high fat diet for life can be considerable.

Studies have shown that several ketones produced in animals and humans have anti-seizure activity in animal models (Hartman et al., *Epilepsia* 49: 334-339, 2008 and Likhodii et al., *Ann. Neurol.* 54:219-226, 2003). Although the anticonvulsant potential of ketones has been well-established, finding a method to translate this activity into a therapy has proven difficult. Typical ketone bodies such as acetone are very short lived and rapidly removed from the body making their use as therapies impractical. Amongst the research in this area are studies showing that specific medium chain fatty acids, such as caprylic acid (octanoic acid), which can be metabolised to ketones have anticonvulsant properties (Chang et al., *Neuropharmacology* 69: 1-10, 2013). Accordingly, caprylic acid, which is used in a medium chain free fatty acid ketogenic diet, has been shown to have anticonvulsant effects (Wlaz et al., *Neuropharmacology* 62: 1882-1889, 2012).

Some ketones have demonstrated the ability to potentiate the anticonvulsant activity of some but not all anti-epileptic drugs (Likhodii et al., *Ann. Neurol.* 54: 219-226, 2003 and Zarnowska et al., *Epilepsia* 50: 1132-1140, 2009). A similar effect has been observed for caprylic acid (Wlaz et al., *Neuropharmacology* 62: 1882-1889, 2012).

The same mechanism which leads to anticonvulsant activity may also produce beneficial cognitive effects. For example, caprylic acid supplementation has been shown to significantly improve cognitive performance in Beagle dogs (Pan et al., *British Journal of Nutrition* 103: 1746-1754, 2010). A similar improvement in cognition following medium chain fatty acids has been reported in diabetic patients (Page et al., *Diabetes* 58: 1237-1244, 2009). In addition, the cognition enhancing effects for compounds with atypical anticonvulsant activities such as piracetam, aniracetam and the well-used anti-epileptic drug levetiracetam are known (Malykh and Sadaie *Drugs* 70: 287-312, 2010 and Genton and Vleyman *Epileptic Disorders* 2: 99-105, 2000).

SUMMARY

Compounds comprising a moiety that leads to the metabolic production of ketones bonded to a ketone-potentiated anti-epileptic drug have been prepared and characterized in the studies of the present application. Compounds of the application decrease the incidence of seizures in CD-1 mice which have received an electrical stimulus to elicit a psychomotor seizure.

Accordingly, the present application includes a compound of Formula I:

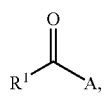

I wherein
A is a ketone-potentiated anti-epileptic drug; and
$R^1$ is $C_{4-15}$alkyl, $C_{4-15}$alkenyl, $C_{3-10}$cycloalkylene$C_{1-10}$alkyl, $C_{5-10}$cycloalkenylene$C_{1-10}$alkyl, $C_{3-10}$cycloalkylene$C_{2-10}$alkenyl or $C_{5-10}$cycloalkenylene$C_{2-10}$alkenyl,
or a pharmaceutically acceptable salt, solvate and/or prodrug thereof.

In an embodiment, A is a ketone-potentiated anti-epileptic γ-aminobutyric acid (GABA) derivative.

In a further embodiment, the compound of Formula I is a compound of Formula I(a):

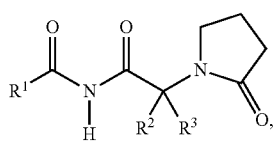

I(a)

wherein
$R^1$ is as defined for the compound of Formula I; and
$R^2$ and $R^3$ are each independently selected from H, $C_{1-8}$alkyl and $C_{2-8}$alkenyl; or $R^2$ and $R^3$ together with the carbon atom to which they are bonded form a $C_{3-10}$cycloalkane or a $C_{5-10}$cycloalkene,
or a pharmaceutically acceptable salt, solvate and/or prodrug thereof.

In another embodiment, the compound of Formula I is a compound of Formula I(b):

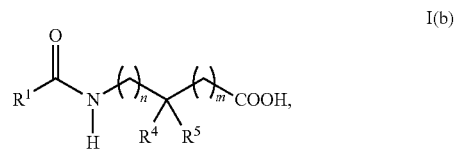

I(b)

wherein
n and m are each independently 0, 1, 2 or 3;
$R^1$ is as defined for the compound of Formula I; and
$R^4$ and $R^5$ are each independently selected from H, $C_{1-8}$alkyl and $C_{2-8}$alkenyl; or
$R^4$ and $R^5$ together with the carbon atom to which they are bonded form a $C_{3-10}$cycloalkane or a $C_{5-10}$cycloalkene,
or a pharmaceutically acceptable salt, solvate and/or prodrug thereof.

The present application also includes a composition comprising one or more compounds of the application and a carrier. In an embodiment, the composition is a pharmaceutical composition comprising one or more compounds of the application and a pharmaceutically acceptable carrier.

In another embodiment, the compounds of the application are used as medicaments. Accordingly, the application also includes one or more compounds of the application for use as a medicament.

The present application includes a method of treating one or more CNS diseases, disorders or conditions selected from epilepsy, non-epileptic seizures, cognitive dysfunction, cognitive performance, anxiety and chronic pain comprising administering one or more compounds of the application to a subject in need thereof. In particular, the present application includes a method of treating epilepsy comprising administering one or more compounds of the application to a subject in need thereof.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

Figure 8:
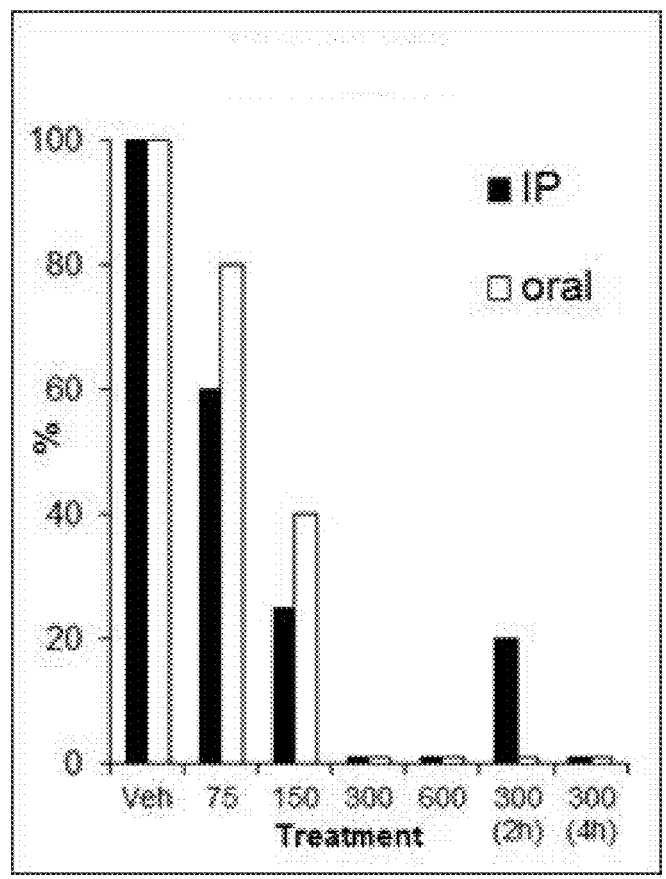

FIG. 8 is a plot showing the effect of compound 20 at doses of 75, 150, 300 or 600 mg/kg given 1 hr pre-stimulation, as well as 300 mg/kg at 2 and 4 hr pre-stimulation, in comparison to a Vehicle ("Veh") control against 6 Hz-induced psychometric seizures, the incidence of which are expressed on the vertical axis as a percentage of the total sample population tested in an exemplary embodiment of the present application. Compound 20 or its vehicle was administered by either oral or intraperitoneal routes of administration. The results are expressed as the incidence of mice displaying at least one behavioural sign characteristic of a psychomotor seizure following each pretreatment.

Figure 9:
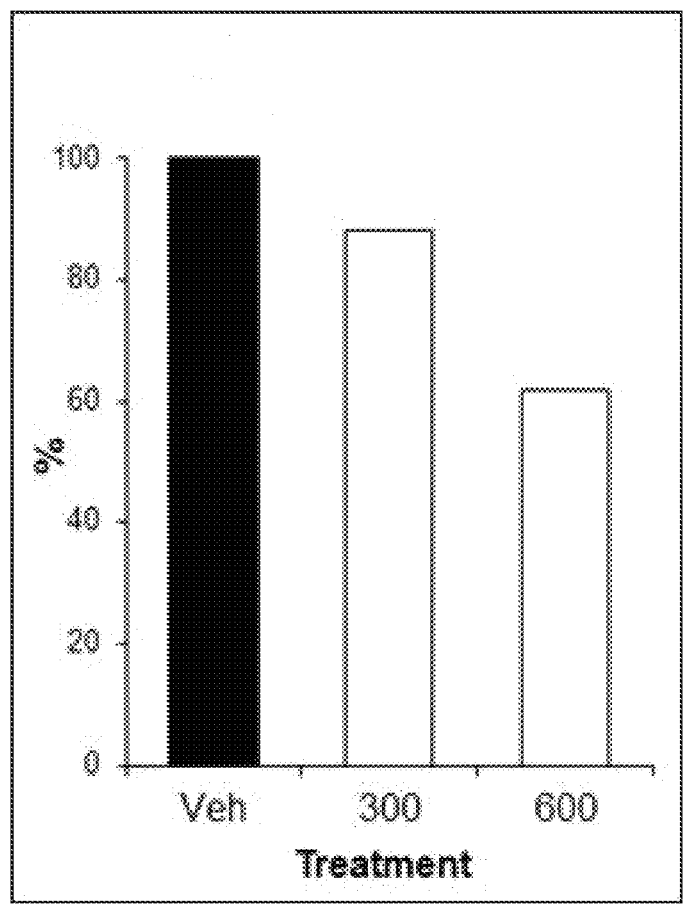

FIG. 9 is a plot showing the effect of compound 20 (300 and 600 mg/kg IP) in comparison to a Vehicle ("Veh") control against scPTZ-induced seizures, the incidence of which are expressed on the vertical axis as a percentage of the total sample population tested in an exemplary embodiment of the present application.

Figure 10:
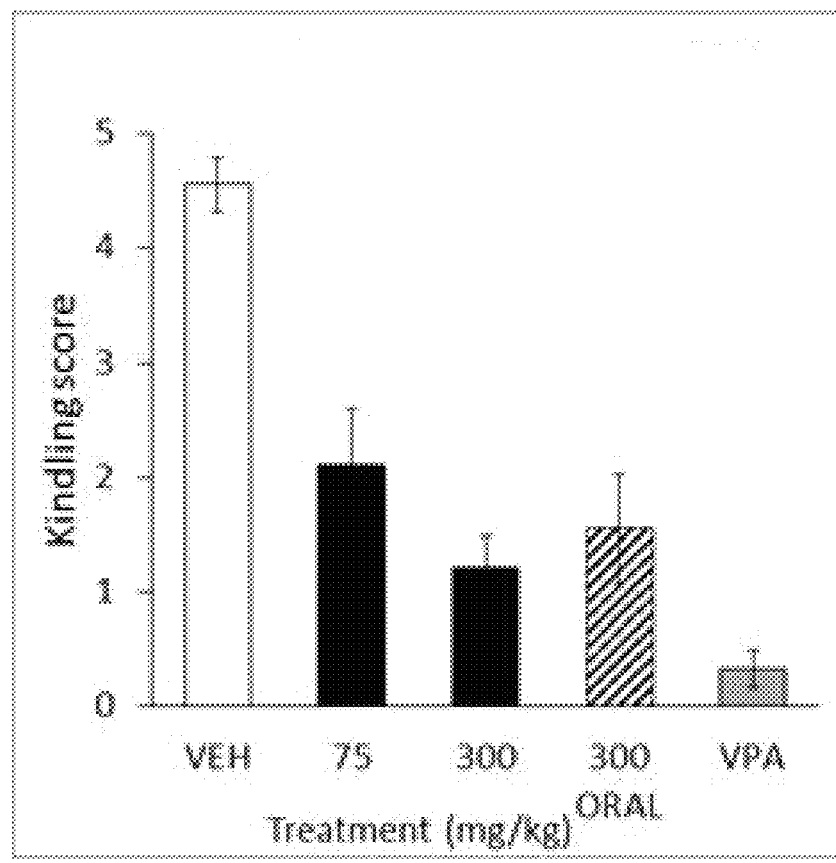

FIG. 10 is a plot showing the effect of compound 20 (75 and 300 mg/kg) pretreatment against corneal kindled seizures in comparison to a Vehicle "Veh" control in an exemplary embodiment of the present application. The vertical axis represents the kindled seizure score according to the Racine (1972) scale. Thus results are expressed as the mean±SEM kindling score following each treatment. Compound 20 was administered by both the IP and oral routes. Sodium Valproate (VPA, 600 mg/kg IP) was also included as a positive control.

Figure 11:
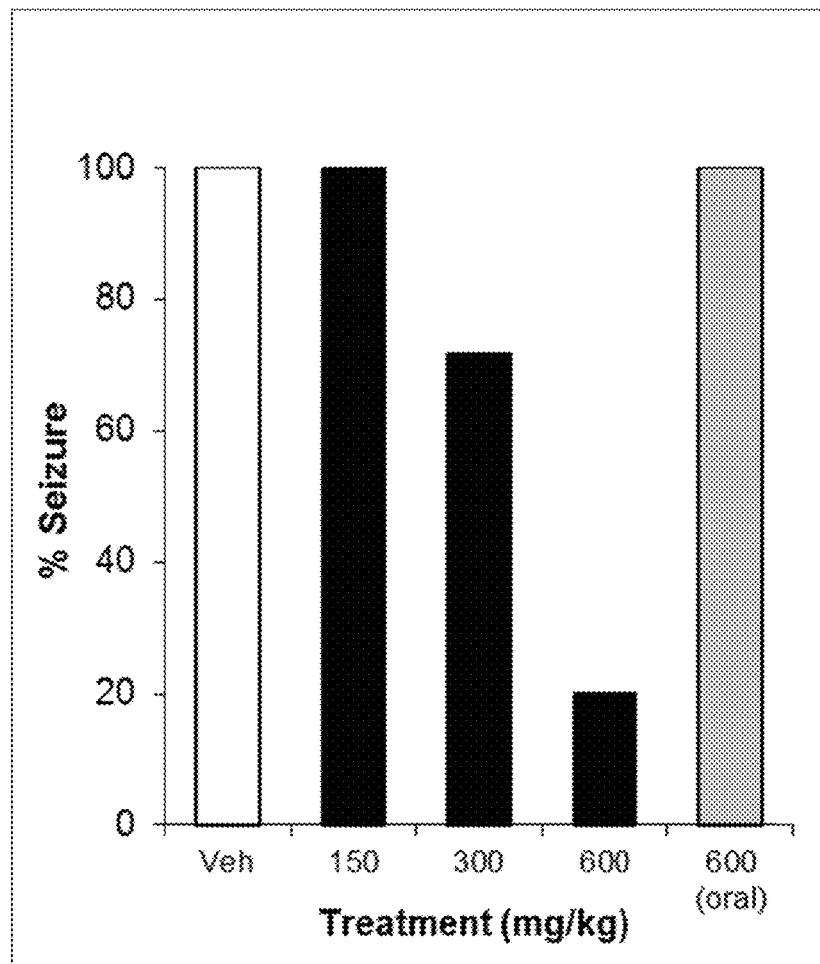

FIG. 11 is a plot showing the effect of compound 25 (150, 300 and 600 mg/kg IP and 600 mg/kg oral) pretreatment in comparison to a Vehicle ("Veh") control against MES-induced tonic seizures, the incidence of which are expressed on the vertical axis as a percentage of the total sample population tested in an exemplary embodiment of the present application.

Figure 12:
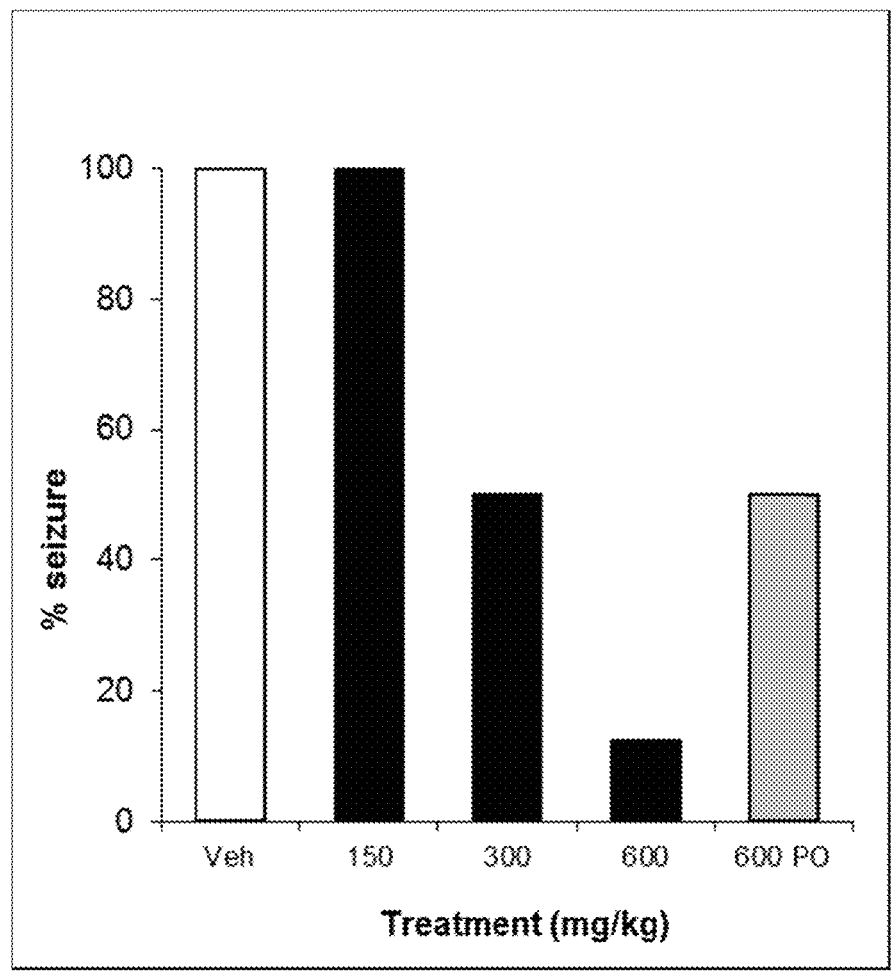

FIG. 12 is a plot showing the effect of compound 25 (150, 300 and 600 mg/kg IP and 600 mg/kg oral) pretreatment in comparison to a Vehicle ("Veh") control against scPTZ-induced seizures, the incidence of which are expressed on the vertical axis as a percentage of the total sample population tested in an exemplary embodiment of the present application.

Figure 13:
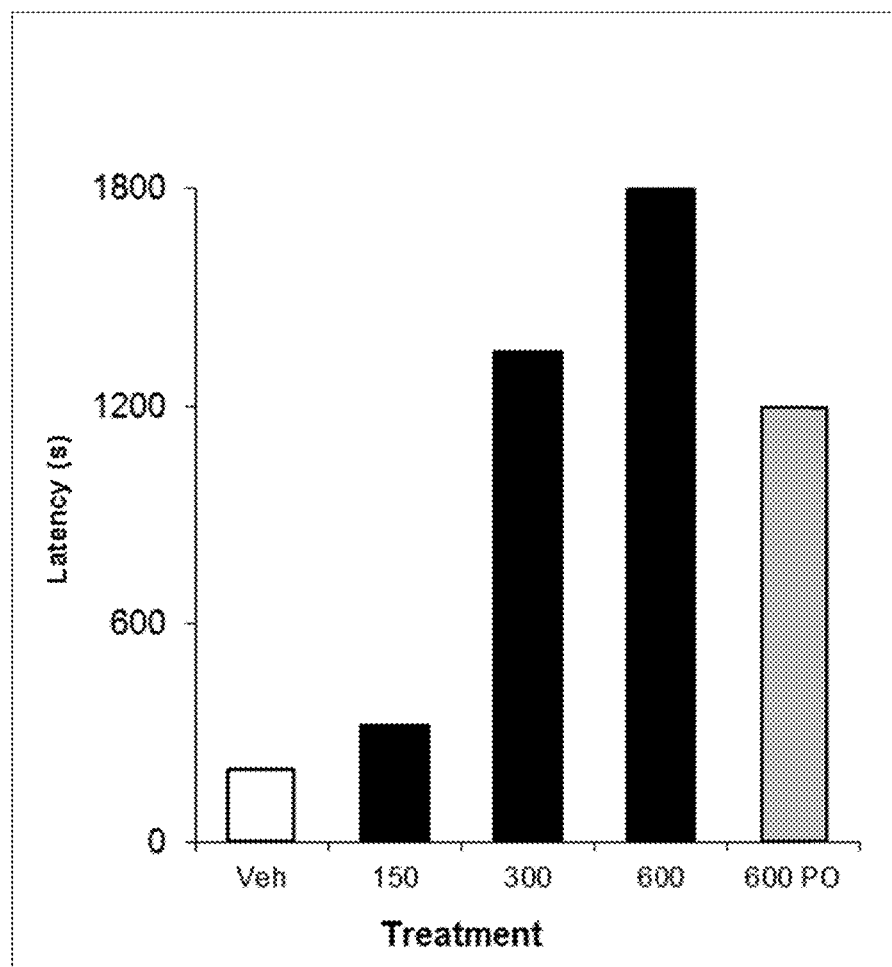

FIG. 13 is a plot showing the effect of compound 25 (150, 300 and 600 mg/kg IP and 600 mg/kg oral) pretreatment in comparison to a Vehicle ("Veh") control against scPTZ-induced seizures in an exemplary embodiment of the present application. The vertical axis shows the onset latency (s) of a seizure from PTZ injection.

Figure 14:
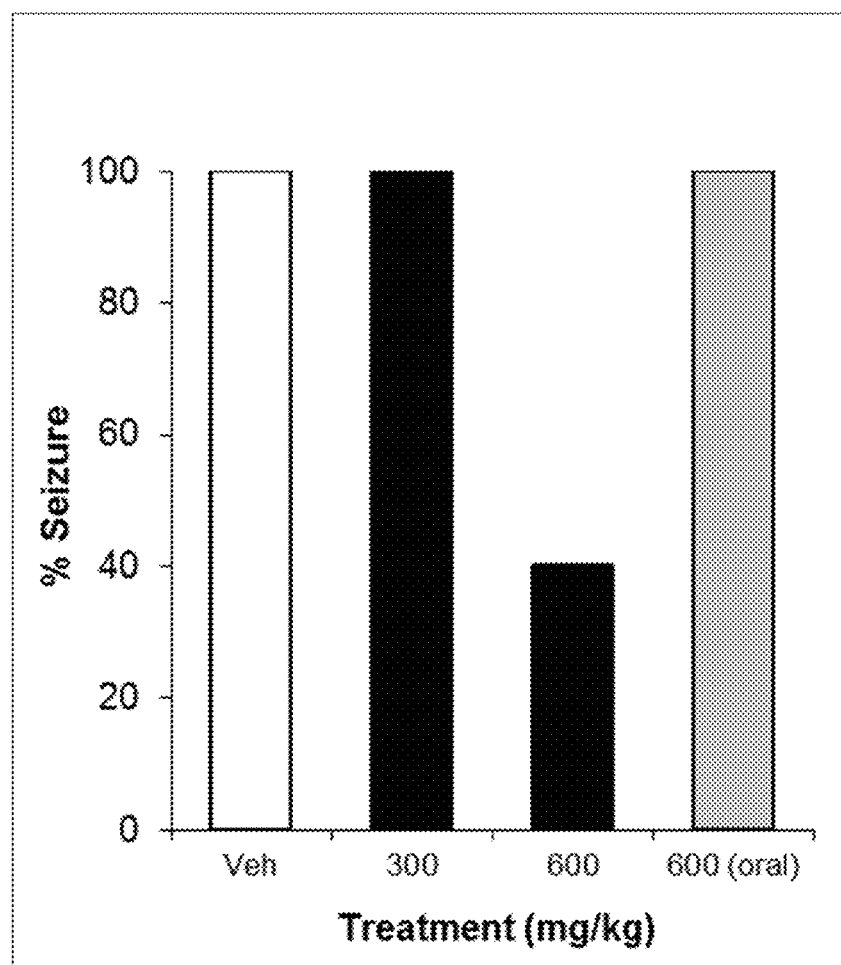

FIG. 14 is a plot showing the effect of compound 26 (300 and 600 mg/kg IP and 600 mg/kg oral) pretreatment in comparison to a Vehicle ("Veh") control against MES-induced tonic seizures, the incidence of which are expressed on the vertical axis as a percentage of the total sample population tested in an exemplary embodiment of the present application.

Figure 15:
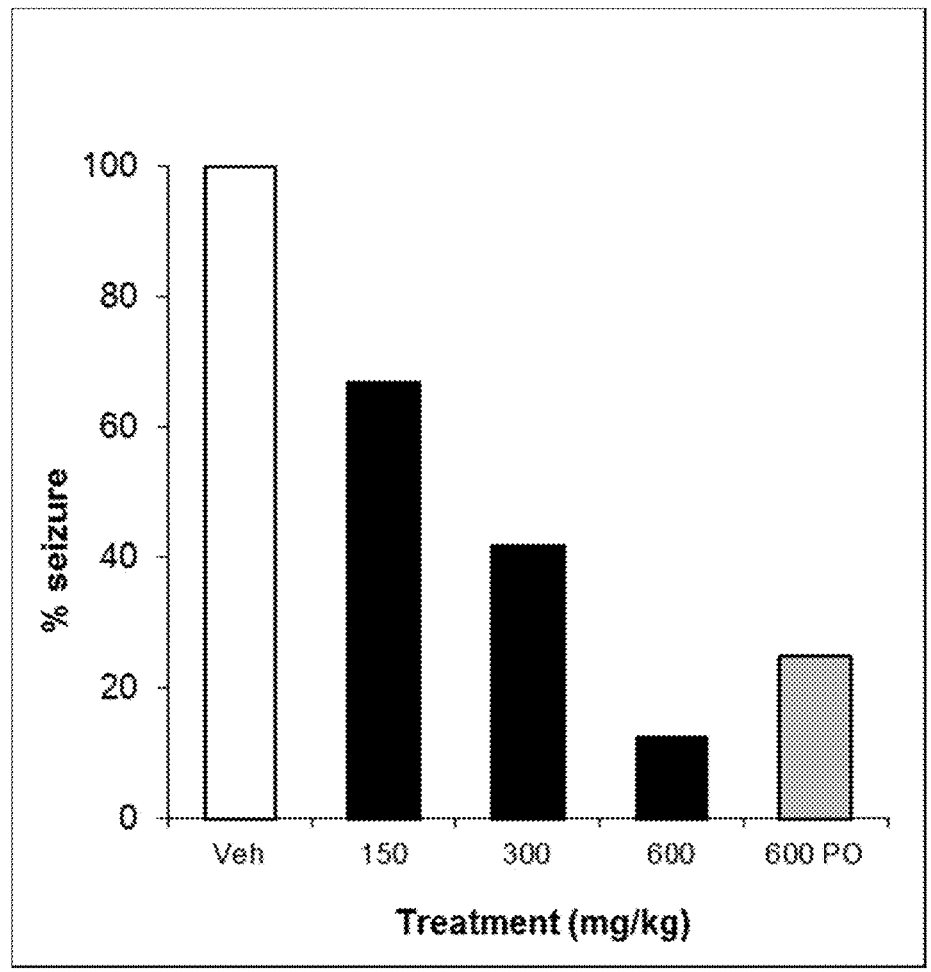

FIG. 15 is a plot showing the effect of compound 26 (150, 300 and 600 mg/kg IP and 600 mg/kg oral) pretreatment in comparison to a Vehicle ("Veh") control against scPTZ-induced seizures, the incidence of which are expressed on the vertical axis as a percentage of the total sample population tested in an exemplary embodiment of the present application.

Figure 16:
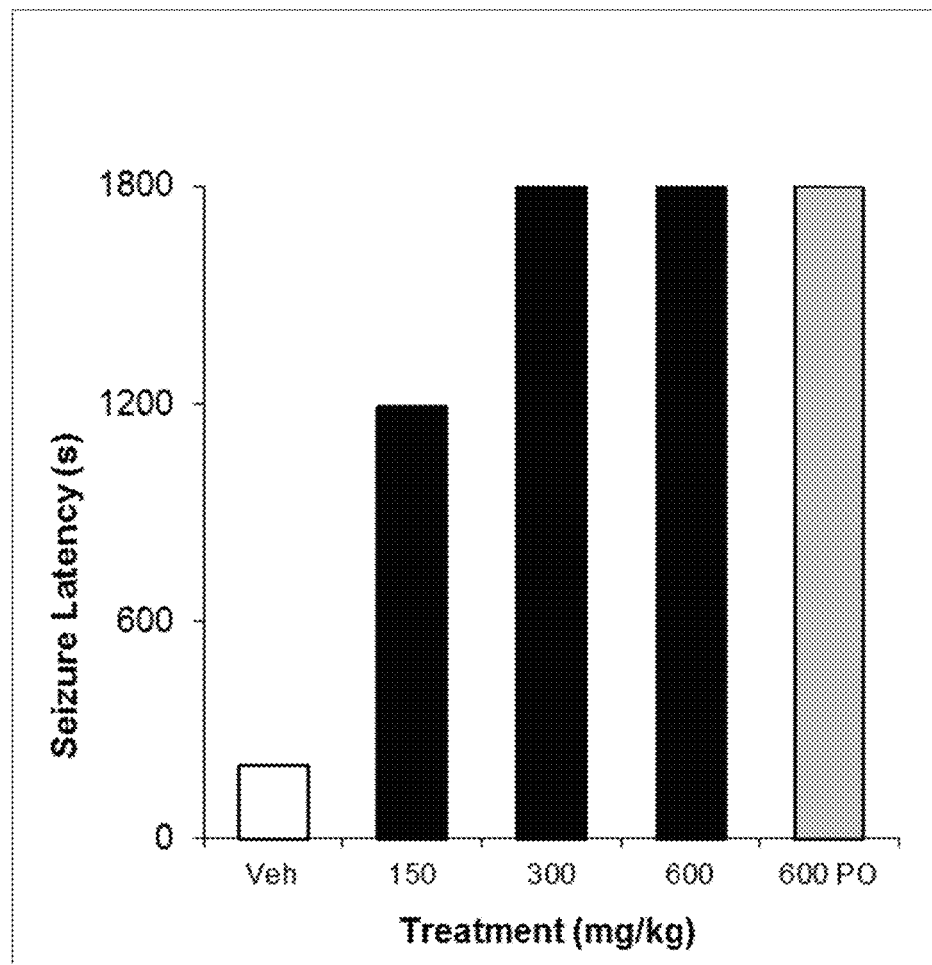

FIG. 16 is a plot showing the effect of compound 26 (150, 300 and 600 mg/kg IP and 600 mg/kg oral) pretreatment in comparison to a Vehicle ("Veh") control against scPTZ-induced seizures in an exemplary embodiment of the present application. The vertical axis shows the onset latency (s) of a seizure from PTZ injection.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present. For example, the expression "pharmaceutically acceptable salt, solvate and/or prodrug thereof" is meant to cover combinations of these various forms of the claimed compounds, including, for example, a solvate of a salt of a compound of Formula I, or a solvate of a salt of a prodrug of a compound of Formula I.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The term "protecting group" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, benzoyl, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

t-Boc as used herein refers to the group t-butyloxycarbonyl.

Ac as used herein refers to the group acetyl.

Ts (tosyl) as used herein refers to the group p-toluenesulfonyl.

Ms as used herein refers to the group methanesulfonyl.

TMS as used herein refers to the group trimethylsilyl.

TBDMS as used herein refers to the group t-butyldimethylsilyl.

TBDPS as used herein refers to the group t-butyldiphenylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-8}$alkyl means an alkyl group having 1, 2, 3, 4, 5, 6, 7 or 8 carbon atoms.

The term "alkenyl" as used herein, whether it is used alone or as part of another group, means straight or branched chain, unsaturated alkenyl groups. The number of carbon atoms that are possible in the referenced alkenyl group are indicated by the numerical prefix "$C_{n1-n2}$". For example, the term $C_{4-15}$alkenyl means an alkenyl group having 4, 5, 6, 7, 8, 9, 10, 11, 12, 13, 14 or 15 carbon atoms and at least one double bond, for example 1 to 3, 1 to 2 or 1 double bond.

The term "cycloalkane" as used herein, whether it is used alone or as part of another group, means a mono- or bicyclic, saturated alkane group. The number of carbon atoms that are possible in the referenced cycloalkane group are indicated by the numerical prefix "$C_{n1-n2}$". For example, the term $C_{3-10}$cycloalkane means a cycloalkane group having 3, 4, 5, 6, 7, 8, 9 or 10 carbon atoms. When a cycloalkane group contains more than one cyclic structure or rings, the cyclic structures are fused, bridged, spiro connected or linked by a single bond.

The term "cycloalkylene" as used herein, whether it is used alone or as part of another group, refers to a bivalent cycloalkane group.

The term "cycloalkene" as used herein, whether it is used alone or as part of another group, means a mono- or bicyclic, unsaturated alkene group. The number of carbon atoms that are possible in the referenced cycloalkene group are indicated by the numerical prefix "$C_{n1-n2}$". For example, the term $C_{5-10}$cycloalkene means a cycloalkene group having 5, 6, 7, 8, 9 or 10 carbon atoms and at least one double bond, for example 1 to 3, 1 to 2 or 1 double bond. When a cycloalkene group contains more than one cyclic structure or rings, the cyclic structures are fused, bridged, spiro connected or linked by a single bond.

The term "cycloalkenylene" as used herein, whether it is used alone or as part of another group, refers to a bivalent cycloalkene group.

A first cyclic structure being "fused" with a second cyclic structure means the first cyclic structure and the second cyclic structure share at least two adjacent atoms therebetween.

A first cyclic structure being "bridged" with a second cyclic structure means the first cyclic structure and the second cyclic structure share at least two non-adjacent atoms therebetween.

A first cyclic structure being "spiro connected" with a second cyclic structure means the first cyclic structure and the second cyclic structure share one atom therebetween.

The term "halo" as used herein refers to a halogen atom and includes F, Cl, Br and I. In an embodiment, halo is Cl, Br or I.

The term "compound of the application" or "compound of the present application" and the like as used herein refers to a compound of Formula I, and pharmaceutically acceptable salts, solvates and/or prodrugs thereof.

The term "disease, disorder or condition of the application" as used herein refers to a disease, disorder or condition for which a compound of the application is useful to treat. In an embodiment, the disease, disorder or condition is a CNS disease, disorder or condition selected from one or more of epilepsy, non-epileptic seizures, cognitive dysfunction, cognitive performance, anxiety and chronic pain.

The term "subject" as used herein includes all members of the animal kingdom including mammals, and suitably refers to humans, companion animals (e.g. dogs, cats, rodents, rabbits etc.) and livestock (e.g. cattle, sheep, pigs, goats, equines such as horses, mules and donkeys etc.).

The term "pharmaceutically acceptable" means compatible with the treatment of subjects such as humans, companion animals and livestock.

The term "pharmaceutically acceptable salt" means an acid addition salt that is suitable for, or compatible with, the treatment of subjects or a base addition salt that is suitable for, or compatible with, the treatment of subjects.

An acid addition salt that is suitable for, or compatible with, the treatment of subjects is any non-toxic organic or inorganic salt of any basic compound. Basic compounds that form an acid addition salt include, for example, compounds comprising an amine group. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of an appropriate salt can be made by a person skilled in the art.

A base addition salt that is suitable for, or compatible with, the treatment of subjects is any non-toxic organic or inorganic base addition salt of any acidic compound. Acidic compounds that form a base addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of an appropriate salt can be made by a person skilled in the art.

The formation of a desired acid addition salt or base addition salt is, for example, achieved using standard techniques. For example, the neutral compound is treated with an acid or base, respectively, in a suitable solvent and the formed salt then isolated by filtration, extraction and/or any other suitable method.

Prodrugs of the compounds of the present application are, for example, conventional esters formed with available amino or carboxyl groups. For example, available amino groups may be acylated using an activated acid in the presence of a base, and optionally, in inert solvent (e.g. an acid chloride in pyridine). Some common esters which have been utilized as prodrugs are phenyl esters, aliphatic ($C_1$-$C_{24}$) esters, acyloxymethyl esters, carbamates and amino acid esters.

The term "solvates" as used herein refers to complexes formed between a compound and a solvent from which the compound is precipitated or in which the compound is made. Accordingly, the term "solvate" as used herein means a compound, or a salt of a compound, wherein molecules of a suitable solvent are incorporated in the crystal lattice. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

In embodiments of the application, the compounds described herein have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

The term "administered" as used herein means administration of an effective amount of one or more compounds of the application to a cell either in cell culture or in a subject.

As used herein, the terms "effective amount" or "therapeutically effective amount" and the like means an amount effective, at dosages and for periods of time necessary to achieve a desired result. For example, in the context of treating epilepsy, an effective amount of the one or more compounds of the application is an amount that, for example, reduces the epilepsy compared to the epilepsy without administration of the one or more compounds of the application. By "reducing the epilepsy", it is meant, for example, reducing the amount and/or frequency of epileptic seizures. Effective amounts may vary according to factors such as the disease state, age, sex, weight and/or species of the subject. The amount of a given compound that will correspond to such an amount will vary depending upon various factors, such as the given compound, the pharmaceutical formulation, the route of administration, the type of condition, disease or disorder being treated, the identity of the subject being treated, and the like, but can nevertheless be routinely determined by one skilled in the art.

The terms "to treat", "treating" and "treatment" as used herein and as is well understood in the art, means an approach for obtaining beneficial or desired results, including clinical results. Beneficial or desired clinical results include, but are not limited to, alleviation or amelioration of one or more symptoms of a disease, disorder or condition of the present application, diminishment of extent of a disease, disorder or condition of the present application, stabilized (i.e. not worsening) state of a disease, disorder or condition of the present application, preventing spread of a disease, disorder or condition of the present application, delay or slowing of the progression of a disease, disorder or condition of the present application, amelioration or palliation of the state of a disease, disorder or condition of the present application, diminishment of the reoccurrence of a disease, disorder or condition of the present application, and remission of a disease, disorder or condition of the present application (whether partial or total), whether detectable or undetectable. "To treat", "treating" and "treatment" can also mean prolonging survival as compared to expected survival if not receiving treatment. "Treating" and "treatment" as used herein also include prophylactic treatment. For example, a subject with early cognitive dysfunction can be treated to prevent progression, or alternatively a subject in remission can be treated with one or more compounds of the application to prevent recurrence. Treating" and "treatment" as used herein also include improving a condition, such as cognitive performance, in the absence of a disease or disorder.

Treatment methods comprise administering to a subject a therapeutically effective amount of one or more compounds of the application, optionally consisting of a single administration, or alternatively comprising a series of administrations. For example, the compounds of the application are administered at least once a week. However, in another embodiment, the compounds are administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, disorder or condition of the present application, the age of the subject, the concentration of the one or more compounds in a formulation, the activity of the compounds of the application, and/or a combination thereof. It will also be appreciated that the effective dosage of a compound used for the treatment may increase or decrease over the course of a particular treatment regime. Changes in dosage may result and become apparent by standard diagnostic assays known in the art. In some instances, chronic administration is required. For example, the one or more compounds of the application are administered in an amount and for a duration sufficient to treat the subject.

"Palliating" a disease, disorder or condition of the present application means that the extent and/or undesirable clinical manifestations of a disease, disorder or condition of the present application state are lessened and/or time course of the progression is slowed or lengthened, as compared to not treating the disease, disorder or condition of the present application.

The term "prevention" or "prophylaxis", or synonym thereto, as used herein refers to a reduction in the risk or probability of a subject becoming afflicted with a disease, disorder or condition of the present application.

The term "ketone-potentiated anti-epileptic drug" as used herein means that the anticonvulsant activity of the drug is potentiated by a ketone.

The term "γ-aminobutyric acid (GABA) derivative" as used herein means a derivative of γ-aminobutyric acid (GABA):

and includes cyclic γ-aminobutyric acid (GABA) derivatives (i.e. derivatives comprising a γ-lactam ring) and linear γ-aminobutyric acid (GABA) derivatives.

II. Compounds and Methods of Preparation Thereof

Compounds comprising a moiety that leads to the metabolic production of ketones bonded to a ketone-potentiated anti-epileptic drug have been prepared and characterized in the studies of the present application.

Accordingly, the present application includes a compound of Formula I:

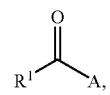

wherein
A is a ketone-potentiated anti-epileptic drug; and
$R^1$ is $C_{4-15}$alkyl, $C_{4-15}$alkenyl, $C_{3-10}$cycloalkylene$C_{1-10}$alkyl, $C_{5-10}$cycloalkenylene$C_{1-10}$alkyl, $C_{3-10}$cycloalkylene$C_{2-10}$alkenyl or $C_{5-10}$cycloalkenylene$C_{2-10}$alkenyl,
or a pharmaceutically acceptable salt, solvate and/or prodrug thereof.

The ketone-potentiated anti-epileptic drug suitably has a functional group that is readily bonded to the moiety that leads to the metabolic production of ketones. For example, ketone-potentiated anti-epileptic drugs having an amino functional group such as but not limited to gabapentin, pregabalin and levetiracetam or protected derivatives thereof are reacted with a precursor (having a C(O)X functional group, wherein X is a leaving group) to the moiety that leads to the metabolic production of ketones under conditions to obtain a compound of the present application. The selection of a suitable ketone-potentiated anti-epileptic drug can be made by a person skilled in the art. In an embodiment, the ketone-potentiated anti-epileptic drug is selected from gabapentin, pregabalin, levetiracetam, vigabatrin, valproate, oxcarbazepine, carbamazepine, progabide, tiagabine, rufinamide, eslicarbazepine, and retigabine.

In an embodiment, A is a ketone-potentiated anti-epileptic γ-aminobutyric acid (GABA) derivative. In another embodiment, the ketone-potentiated anti-epileptic γ-aminobutyric acid (GABA) derivative is selected from gabapentin, pregabalin, levetiracetam and vigabatrin. In a further embodiment, the ketone-potentiated anti-epileptic γ-aminobutyric acid (GABA) derivative is selected from gabapentin, pregabalin, levetiracetam and vigabatrin, each of which is covalently bonded to the $R^1C(O)$ group of the compound of Formula I via an amino group. It is an embodiment that the ketone-potentiated anti-epileptic γ-aminobutyric acid (GABA) derivative is selected from gabapentin, pregabalin and levetiracetam, each of which is covalently bonded to the $R^1C(O)$ group of the compound of Formula I via an amino group.

In a further embodiment, the compound of Formula I is a compound of Formula I(a):

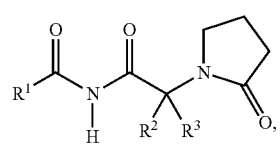

wherein
$R^1$ is as defined for the compound of Formula I; and
$R^2$ and $R^3$ are each independently selected from H, $C_{1-8}$alkyl and $C_{2-8}$alkenyl; or
$R^2$ and $R^3$ together with the carbon atom to which they are bonded form a $C_{3-10}$cycloalkane or a $C_{5-10}$cycloalkene,
or a pharmaceutically acceptable salt, solvate and/or prodrug thereof.

In an embodiment, at least one of $R^2$ and $R^3$ is $C_{1-8}$alkyl or $C_{2-8}$alkenyl. In another embodiment, at least one of $R^2$ and $R^3$ is $C_{1-8}$alkyl. In a further embodiment, at least one of $R^2$ and $R^3$ is $C_{1-6}$alkyl. It is an embodiment that at least one of $R^2$ and $R^3$ is $C_{1-4}$alkyl. In another embodiment of the present application, at least one of $R^2$ and $R^3$ is ethyl.

In an embodiment, $R^2$ is H and $R^3$ is $C_{1-8}$alkyl or $C_{2-8}$alkenyl. In another embodiment, $R^2$ is H and $R^3$ is $C_{1-8}$alkyl. In a further embodiment, $R^2$ is H and $R^3$ is $C_{1-6}$alkyl. It is an embodiment that $R^2$ is H and $R^3$ is $C_{1-4}$alkyl. In another embodiment of the present application, $R^2$ is H and $R^3$ is ethyl.

In another embodiment, A has the structure:

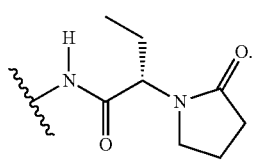 [SMILES: *NC(=O)[C@H](CC)N1CCCC1=O]

In an embodiment, both $R^2$ and $R^3$ are H.

In another embodiment, the compound of Formula I is a compound of Formula I(b):

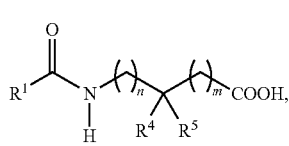

wherein n and m are each independently 0, 1, 2 or 3;

$R^1$ is as defined for the compound of Formula I; and $R^4$ and $R^5$ are each independently selected from H, $C_{1-8}$alkyl and $C_{2-8}$alkenyl; or $R^4$ and $R^5$ together with the carbon atom to which they are bonded form a $C_{3-10}$cycloalkane or a $C_{5-10}$cycloalkene, or a pharmaceutically acceptable salt, solvate and/or prodrug thereof.

In another embodiment, n+m=2. In a further embodiment, both n and m are 1. It is an embodiment that n is 2 and m is 0. In another embodiment of the present application, n is 0 and m is 2.

In an embodiment, at least one of $R^4$ and $R^5$ is $C_{1-8}$alkyl or $C_{2-8}$alkenyl. In another embodiment, at least one of $R^4$ and $R^5$ is $C_{1-6}$alkyl or $C_{2-6}$alkenyl. In a further embodiment, at least one of $R^4$ and $R^5$ is $C_{1-6}$alkyl. It is an embodiment that at least one of $R^4$ and $R^5$ is 2-methylpropyl (isobutyl). In another embodiment of the present application, at least one of $R^4$ and $R^5$ is $C_{2-6}$alkenyl. In a further embodiment, at least one of $R^4$ and $R^5$ is vinyl.

In an embodiment, $R^4$ is H and $R^5$ is $C_{1-8}$alkyl or $C_{2-8}$alkenyl. In another embodiment, $R^4$ is H and $R^5$ is $C_{1-6}$alkyl or $C_{2-6}$alkenyl. In a further embodiment, $R^4$ is H and $R^5$ is $C_{1-6}$alkyl. It is an embodiment that $R^4$ is H and $R^5$ is 2-methylpropyl (isobutyl). In another embodiment of the present application, $R^4$ is H and $R^5$ is $C_{2-6}$alkenyl. In a further embodiment, $R^4$ is H and $R^5$ is vinyl.

In an embodiment, A has the structure:

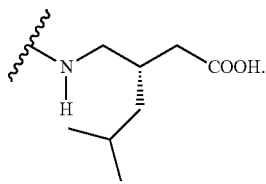 [SMILES: *NC[C@H](CC(=O)O)CC(C)C]

In another embodiment, A has the structure:

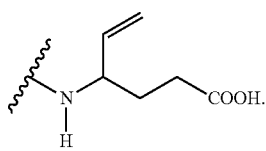 [SMILES: *NC(C=C)CCC(=O)O]

In an embodiment, $R^4$ and $R^5$ together with the carbon atom to which they are bonded form a $C_{3-10}$cycloalkane or a $C_{5-10}$cycloalkene. In another embodiment, $R^4$ and $R^5$ together with the carbon atom to which they are bonded form a $C_{3-10}$cycloalkane. In a further embodiment, $R^4$ and $R^5$ together with the carbon atom to which they are bonded form a $C_{5-8}$cycloalkane. It is an embodiment that A has the structure:

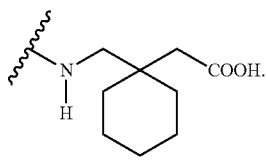 [SMILES: *NCC1(CC(=O)O)CCCCC1]

In an embodiment, $R^1$ is $C_{4-15}$alkyl, $C_{4-15}$alkenyl, $C_{3-10}$cycloalkylene$C_{1-10}$alkyl or $C_{3-10}$cycloalkylene$C_{2-10}$alkenyl. In another embodiment, $R^1$ is $C_{6-12}$alkyl, $C_{6-12}$alkenyl, $C_{3-8}$cycloalkylene$C_{1-8}$alkyl or $C_{3-8}$cycloalkylene$C_{1-8}$alkenyl. In a further embodiment, $R^1$ is $C_{5-11}$alkyl or $C_{5-11}$alkenyl. In an embodiment, $R^1$ is $C_{4-15}$alkyl. It is an embodiment that $R^1$ is $C_{6-12}$alkyl. In a further embodiment, $R^1$ is $C_{5-11}$alkyl. In another embodiment, $R^1$ is $C_{3-8}$cycloalkylene$C_{1-8}$alkyl. In a further embodiment, $R^1$ is cyclohexylene$C_{1-8}$alkyl. It is an embodiment that $R^1$ is

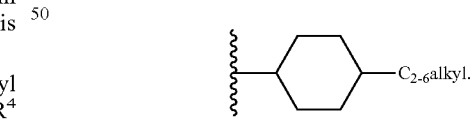

In an embodiment, $R^1$ is selected from n-pentyl, n-hexyl, n-heptyl, n-octyl, n-nonyl, n-decyl, n-undecyl, 3-methylheptyl, 1-propylbutyl, 3-ethylheptyl and 4-butylcyclohexyl. In another embodiment, $R^1$ is selected from n-pentyl, n-hexyl, n-heptyl, n-octyl, n-nonyl, n-decyl, n-undecyl, 3-methylheptyl and 1-propylbutyl. In a further embodiment, $R^1$ is n-heptyl, n-octyl, n-nonyl, 3-ethylheptyl or 4-butylcyclohexyl. In another embodiment, $R^1$ is n-heptyl, n-octyl or n-nonyl. In a further embodiment, $R^1$ is n-heptyl. It is an embodiment that $R^1$ is n-octyl. In another embodiment, $R^1$ is n-nonyl. It is an embodiment that $R^1$ is 3-ethylheptyl. In another embodiment of the present application, $R^1$ is 4-butylcyclohexyl.

In an embodiment, the compound of Formula I is selected from:
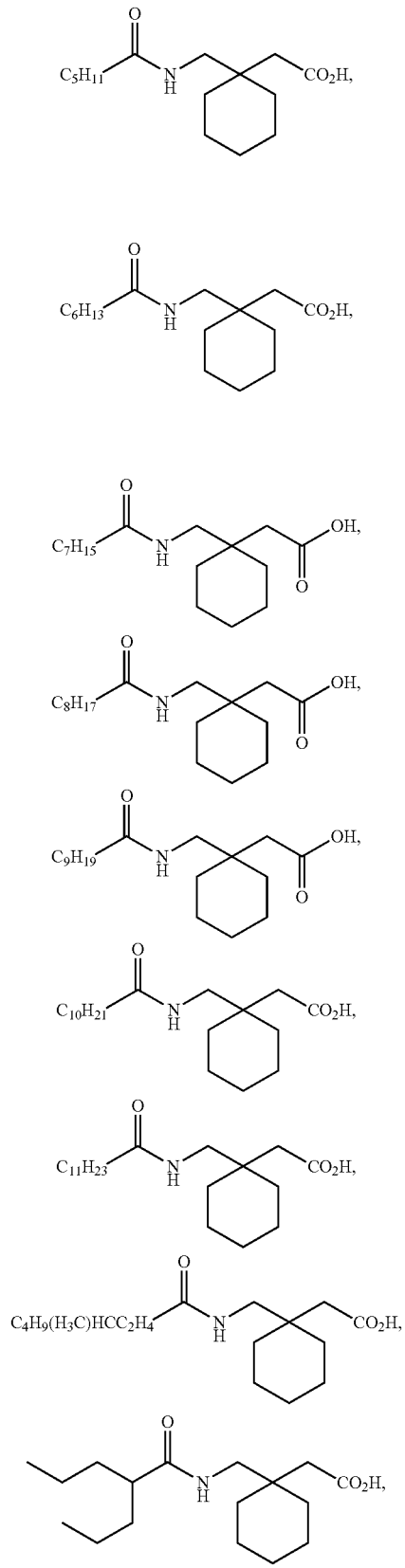
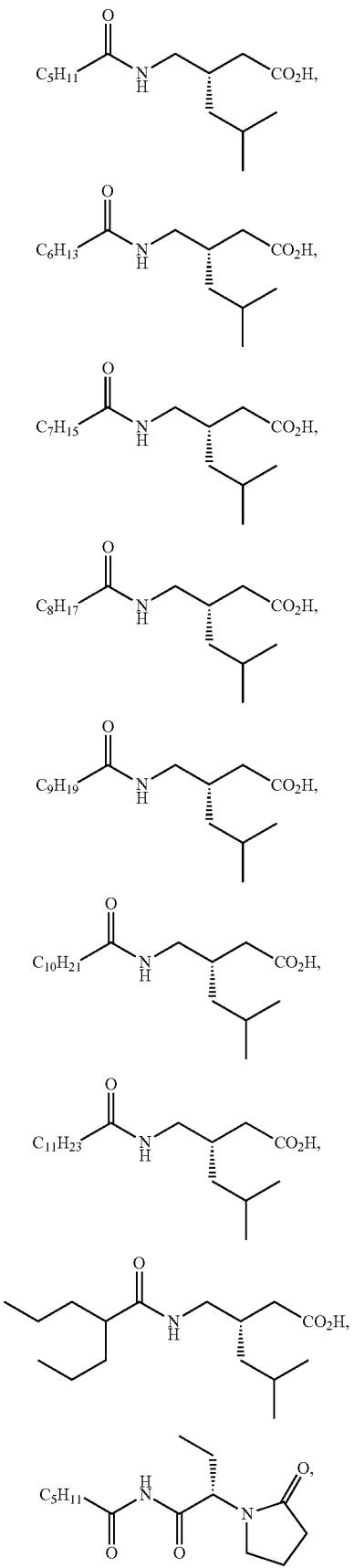

-continued
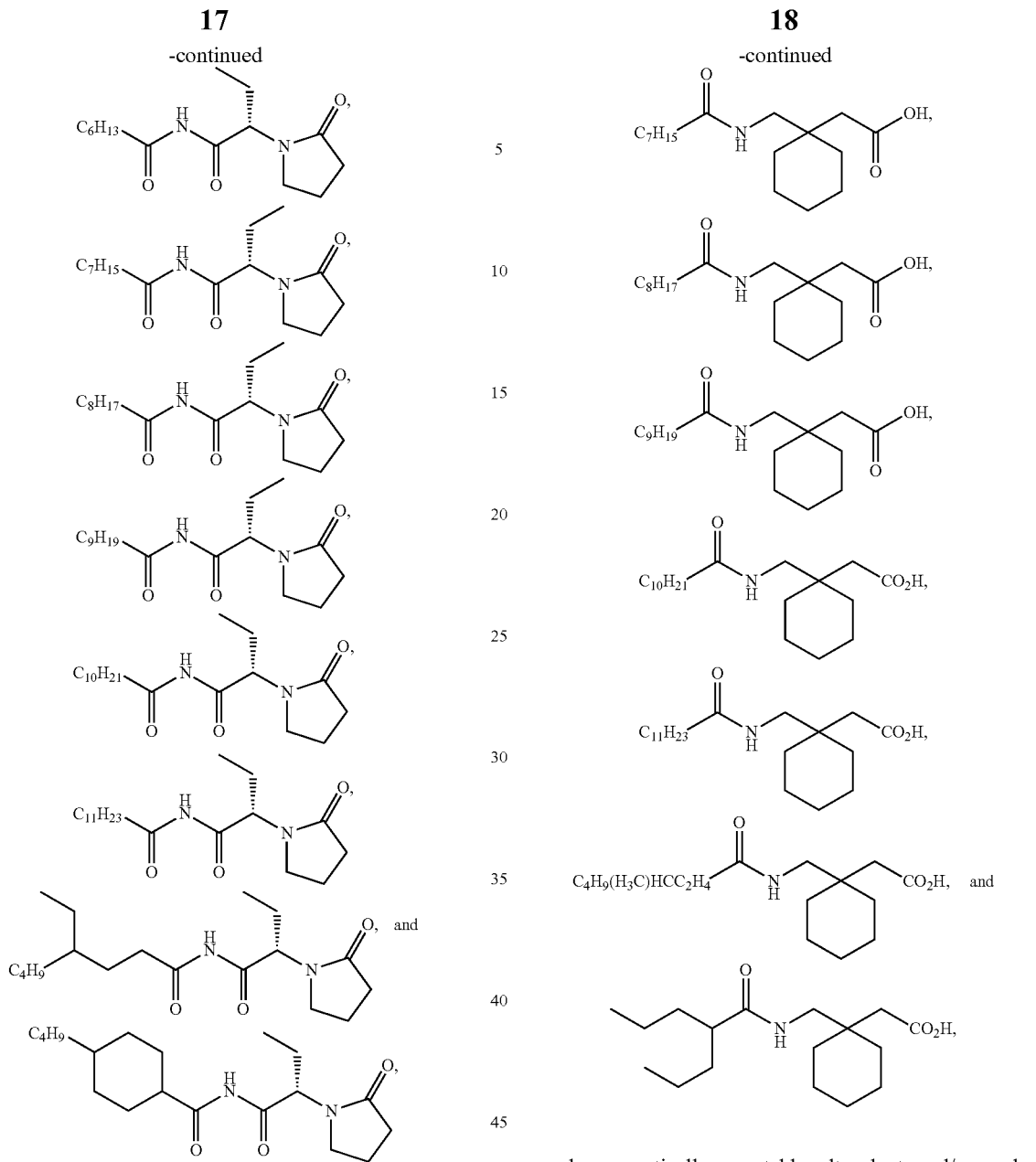
or a pharmaceutically acceptable salt, solvate and/or prodrug thereof.
In an embodiment, the compound of Formula I is selected from:
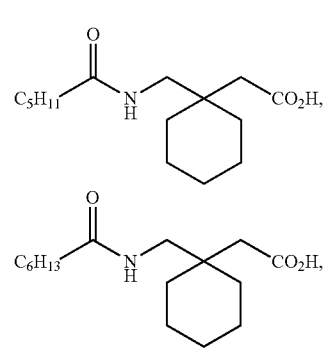
or a pharmaceutically acceptable salt, solvate and/or prodrug thereof.
In an embodiment, the compound of Formula I is selected from:
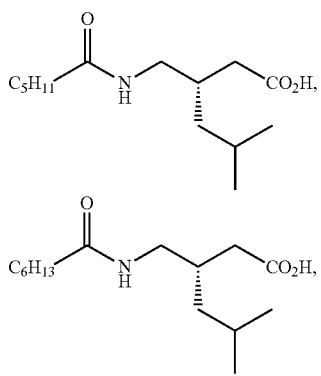

-continued
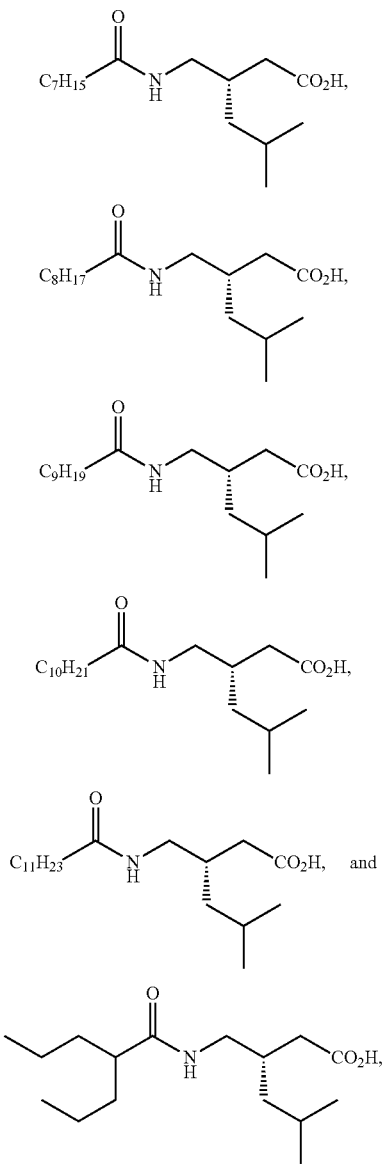
or a pharmaceutically acceptable salt, solvate and/or prodrug thereof.
In an embodiment, the compound of Formula I is selected from:
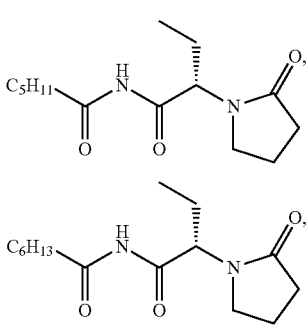
-continued
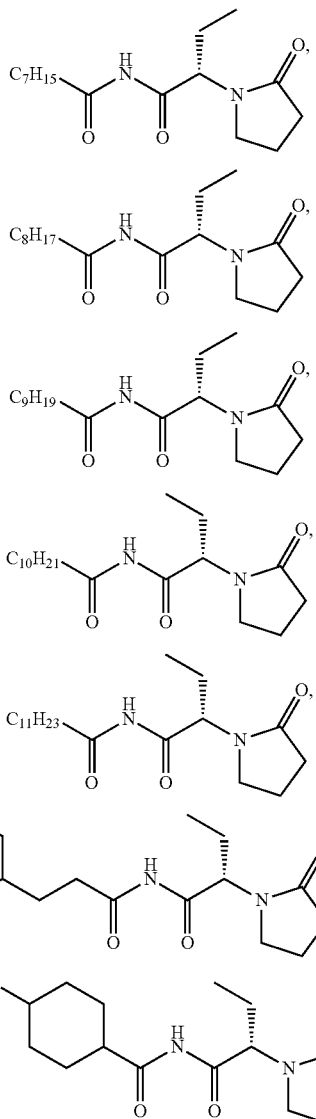
or a pharmaceutically acceptable salt, solvate and/or prodrug thereof.
In an embodiment, the compound of Formula I is selected from:
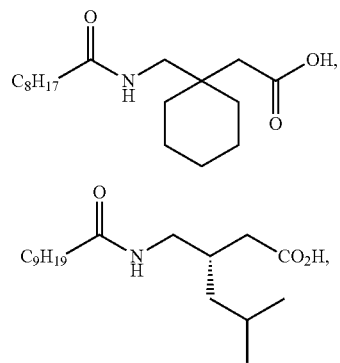

-continued

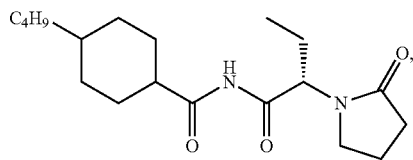

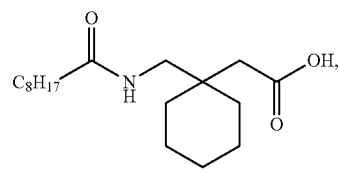

or a pharmaceutically acceptable salt, solvate and/or prodrug thereof.

In an embodiment, the compound of Formula I is:

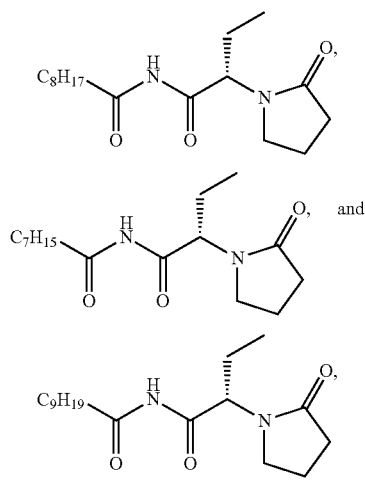

or a pharmaceutically acceptable salt, solvate and/or prodrug thereof.

In another embodiment, the compound of Formula I is:

or a pharmaceutically acceptable salt, solvate and/or prodrug thereof.

In another embodiment, the compound of Formula I is selected from:

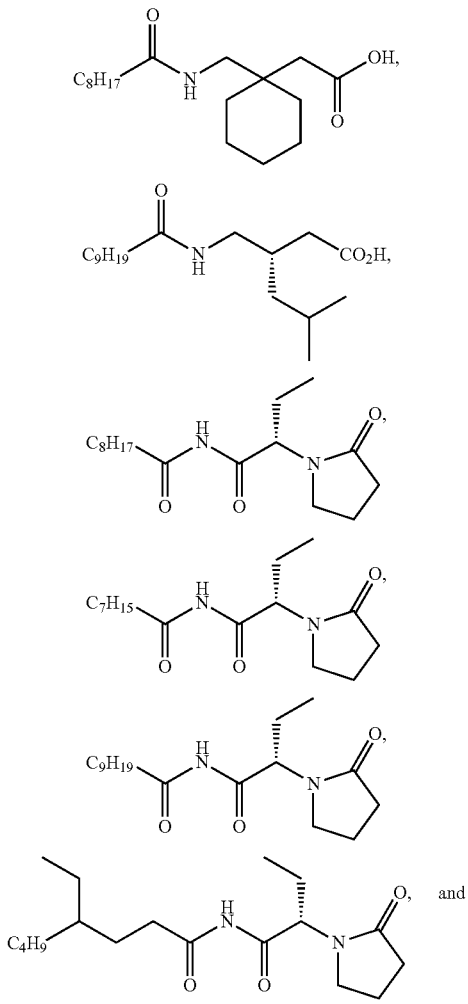

or a pharmaceutically acceptable salt, solvate and/or prodrug thereof.

In a further embodiment, the compound of Formula I is:

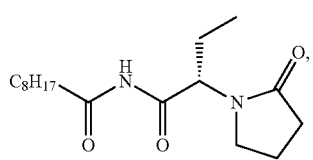

or a pharmaceutically acceptable salt, solvate and/or prodrug thereof.

It is an embodiment that the compound of Formula I is:

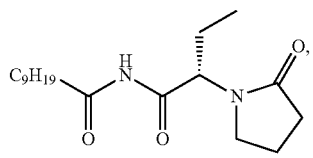

or a pharmaceutically acceptable salt, solvate and/or prodrug thereof.

In another embodiment, the compound of Formula I is:

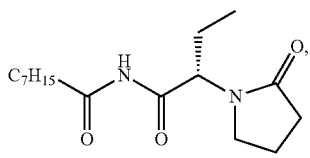

or a pharmaceutically acceptable salt, solvate and/or prodrug thereof.

In a further embodiment, the compound of Formula I is:

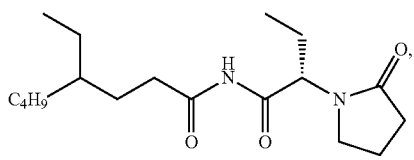

or a pharmaceutically acceptable salt, solvate and/or prodrug thereof.

In another embodiment of the present application, the compound of Formula I is selected from:

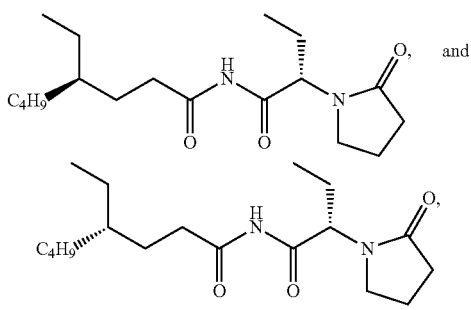

or a pharmaceutically acceptable salt, solvate and/or prodrug thereof.

In an embodiment, the compound of Formula I is:

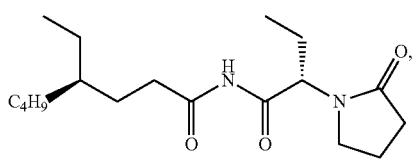

or a pharmaceutically acceptable salt, solvate and/or prodrug thereof.

In another embodiment, the compound of Formula I is:

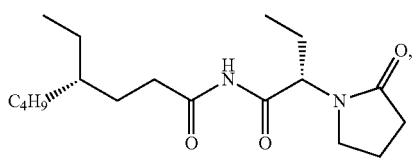

or a pharmaceutically acceptable salt, solvate and/or prodrug thereof.

It is an embodiment that the compound of Formula I is:

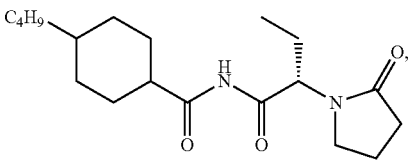

or a pharmaceutically acceptable salt, solvate and/or prodrug thereof.

In another embodiment of the present application, the compound of Formula I is selected from:

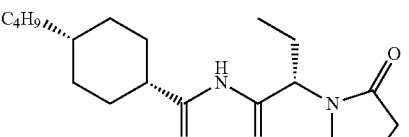

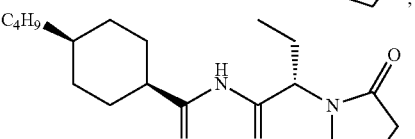

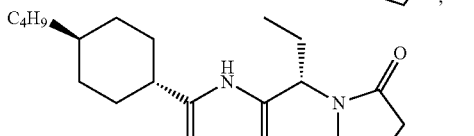

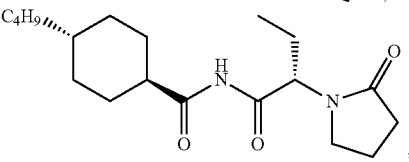

or a pharmaceutically acceptable salt, solvate and/or prodrug thereof.

In another embodiment, the compound of Formula I is:

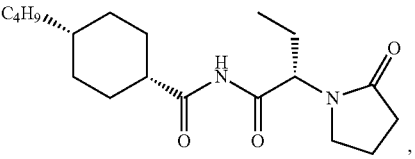

or a pharmaceutically acceptable salt, solvate and/or prodrug thereof.

In a further embodiment, the compound of Formula I is:

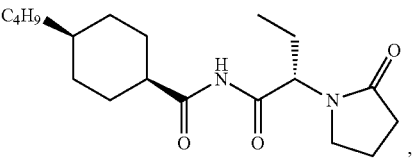

or a pharmaceutically acceptable salt, solvate and/or prodrug thereof.

In another embodiment, the compound of Formula I is:

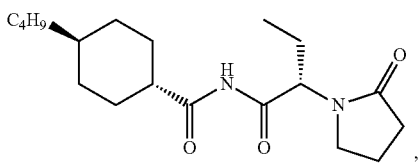

or a pharmaceutically acceptable salt, solvate and/or prodrug thereof.

In a further embodiment, the compound of Formula I is:

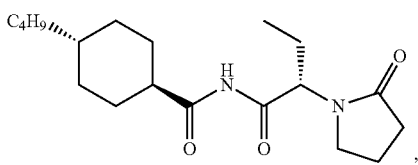

or a pharmaceutically acceptable salt, solvate and/or prodrug thereof.

In another embodiment of the present application, the compound of Formula I is selected from:

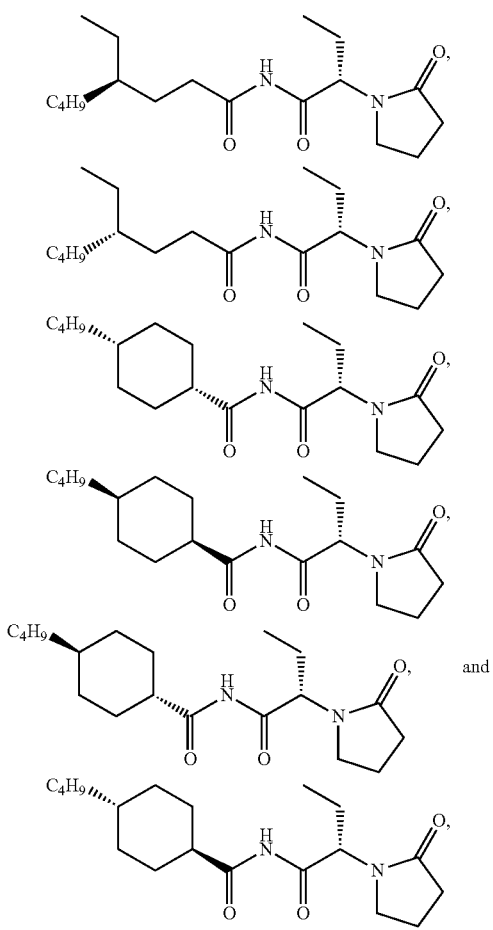

or a pharmaceutically acceptable salt, solvate and/or prodrug thereof.

The compounds of the application are prepared by processes analogous to those established in the art, for example, by the reaction sequences shown in general synthetic schemes 1-2.

In an embodiment of the application, a compound of Formula I(a) is prepared under suitable standard alkylating conditions by treating a compound of Formula II(a) with a compound of Formula IV, or a suitably protected derivative thereof, wherein $R^1$, $R^2$ and $R^3$ are as defined herein for the compounds of the present application and X is a leaving group such as halogen e.g., a chloro, bromo or iodo-group, under conditions to form the compound of Formula I(a), as shown in Scheme 1.

Scheme 1

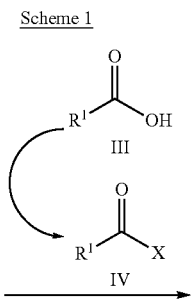

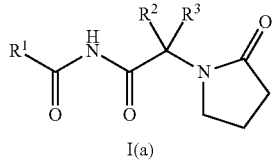

Conditions to effect the alkylation of the compound of Formula II(a) with a compound of Formula IV include reacting at room temperature or heating with or without a solvent, for example with a suitable solvent such as THF, DMF, DMSO, or diethyl ether, in the presence of a base such as but not limited to DMAP, NaH, ⁱBuOK, ⁱBuONa, pyridine, or diisopropyl ethylamine. If the compound of Formula IV is not commercially available, it can be prepared from the corresponding acid of Formula III under suitable conditions for the formation of the compound of Formula IV; i.e. with or without heating, either without a solvent or in the presence of a suitable solvent such as $CH_2Cl_2$ or DMSO, in the presence of a reagent such as thionyl chloride or oxalyl chloride (Scheme 1).

Similarly, in another embodiment of the application, the compound of Formula I(b), wherein n, m, $R^1$, $R^4$ and $R^5$ are as defined herein for the compounds of the present application, is prepared, for example, from a compound of Formula II(b) under conditions comprising using a suitable solvent such as DMF, DMSO, THF or diethyl ether in presence of a suitable base such as but not limited to NaH, ⁱBuOK, ⁱBuONa, pyridine or DMAP, as shown in Scheme 2.

Scheme 2

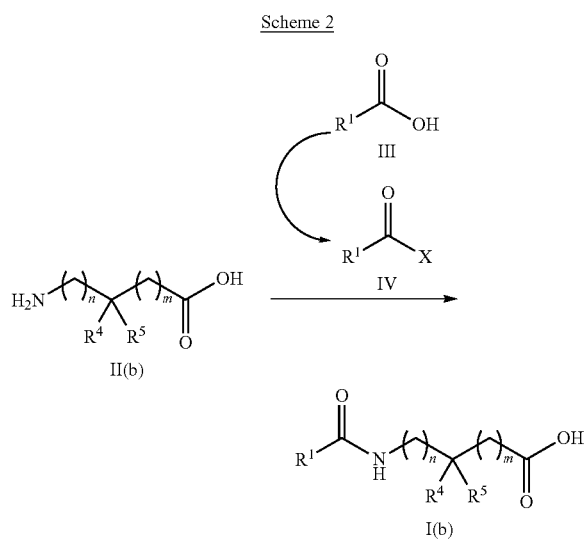

In some embodiments of the present application, the chemistry outlined above is modified, for example by the use of a suitable protecting group for the carboxylic acid moiety in the compounds of Formula I(b) to prevent side reactions. This is achieved, for example by means of conventional protecting groups as described, for example, in *Greene's protective groups in organic synthesis*, P. G. M. Wuts and T. W. Greene, John Wiley & Sons, 2012.

The compounds of the application and their intermediates are isolatable from their reaction mixtures and purifiable using conventional laboratory techniques including, for example, solvent extraction, column chromatography using silica gel as well as alumina, distillation, crystallization, recrystallization and/or chiral separation.

The formation of a desired salt of the compounds of the present application is achieved using standard techniques. For example, a basic addition salt is prepared by treating a neutral compound with a base such as NaOH or KOH in a suitable solvent and the salt isolated by filtration, extraction, and/or evaporation of solvent or any other suitable method.

Preparation of an optical isomer of a compound of the application is performed, for example by the reaction of the appropriate optically active starting material under reaction conditions which will not cause racemization or alternatively the individual enantiomer or diastereomer (with more than one chiral center) is isolated by the separation of a racemic mixture using standard techniques such as fractional crystallization, chiral salt formation and/or chiral HPLC separation.

III. Compositions

The present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier.

The compounds of the application can be administered to a subject in a variety of forms depending on the selected route of administration, as will be understood by those skilled in the art. In an embodiment, the one or more compounds of the application are administered to the subject, or used, by oral (including sublingual and buccal) or parenteral (including intravenous, intraperitoneal, subcutaneous, intramuscular, transepithelial, nasal, intrapulmonary, intrathecal, rectal, topical, patch, pump and transdermal) administration and the compound(s) formulated accordingly. For example, the compounds of the application are administered by injection, in a spray, in a tablet/caplet, in a powder, topically, in a gel, in drops, by a patch, by an implant, by a slow release pump or by any other suitable method of administration, the selection of which can be made by a person skilled in the art.

In an embodiment, the one or more compounds of the application are orally administered, for example, with an inert diluent or with an assimilable edible carrier, or enclosed in hard or soft shell gelatin capsules, or compressed into tablets, or incorporated directly with the food of the diet. In an embodiment, for oral therapeutic administration, the one or more compounds of the application are incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In an embodiment, liposomes are formed from a variety of phospholipids, such as cholesterol, stearylamine and/or phosphatidylcholines.

In another embodiment of the application, the one or more compounds of the application are freeze dried and the lyophilizates obtained, are used for example, for the preparation of products for injection.

In another embodiment, the one or more compounds of the application are administered parenterally. Solutions of the one or more compounds of the application are, for example, prepared in water suitably mixed with a surfactant such as hydroxypropylcellulose. In a further example, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists.

Compositions for nasal administration are, for example, conveniently formulated as aerosols, drops, gels or powders. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas, such as compressed air or an organic propellant such as a fluorochlorohydrocarbon. In another embodiment, the aerosol dosage forms take the form of a pump-atomizer.

Compositions suitable for buccal or sublingual administration include tablets, lozenges, and pastilles, wherein the active ingredient is formulated with a carrier such as sugar, acacia, tragacanth, gelatin and/or glycerine. Compositions for rectal administration are, for example, conveniently in the form of suppositories containing a conventional suppository base such as cocoa butter.

In another embodiment, the one or more compounds of the application are coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. In another embodiment, the one or more compounds of the application are coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

IV. Methods of Treatment and Uses

The compounds of the present application are new therefore, the present application includes all uses for compounds of the application, including use in therapeutic methods, diagnostic assays, and as research tools whether alone or in combination with another active pharmaceutical ingredient.

The compounds of the application have been shown to decrease the incidence of seizures in CD-1 mice which have received an electrical stimulus to elicit a psychomotor seizure. The compounds of the application comprise known and atypical anticonvulsant moieties which operate alone or together (additively or synergistically) to suppress seizure activity as manifested by physical symptoms and/or electrical activity of the brain as measured by EEG or other standard methods of measurement. Combining a relevant anticonvulsant moiety i.e. one that is potentiated by a ketone, with a moiety which leads to the metabolic production of ketones and related species, including medium chain free fatty acids, in one structure provides a mechanism to develop a unique series of dual action anticonvulsant drugs. In an embodiment, the compounds of the application act as carriers and pro-drugs for each anticonvulsant element therein.

Therefore, in one embodiment, the compounds of the present application are useful as medicaments. Accordingly, the present application includes one or more compounds of the application for use as a medicament. In a further embodiment, the compounds of the application are useful for treating CNS diseases, disorders or conditions such as one or more of epilepsy, non-epileptic seizures, cognitive dysfunction, cognitive performance, anxiety, and chronic pain in subjects such as humans and animals.

Accordingly, the present application includes a method of treating epilepsy comprising administering one or more compounds of the application to a subject in need thereof. The present application also includes a use of one or more compounds of the application for treating epilepsy in a subject; a use of one or more compounds of the application for preparation of a medicament for treating epilepsy in a subject; and one or more compounds of the application for use to treat epilepsy in a subject.

In an embodiment, the compounds of the application are useful as an adjunct therapy with other epilepsy treatments such as anti-epileptic drugs and ketogenic (i.e. high fat, low carbohydrate) diets. Accordingly, the present application includes a method of treating epilepsy comprising administering, to a subject in need thereof, one or more compounds of the application in combination with an adjunct epilepsy treatment. The present application also includes a use of one or more compounds of the application in combination with an adjunct epilepsy treatment for treating epilepsy in a subject; a use of one or more compounds of the application in combination with an adjunct epilepsy treatment for preparation of a medicament for treating epilepsy in a subject; and one or more compounds of the application in combination with an adjunct epilepsy treatment for use to treat epilepsy in a subject. In an embodiment, the adjunct epilepsy treatment is a ketogenic diet. In another embodiment, the adjunct epilepsy treatment is an anti-epileptic drug.

In an embodiment, the administration or use of a compound of the application in combination with an anti-epileptic drug reduces the dose of the anti-epileptic drug that is effective for treatment of epilepsy. In another embodiment, the administration or use of a compound of the application in combination with a ketogenic diet reduces the fat:carbohydrate ratio that is effective for treatment of epilepsy and thereby makes the ketogenic diet more tolerable to the subject.

In an embodiment, the epilepsy is symptomatic epilepsy. In another embodiment, the epilepsy is idiopathic epilepsy. In a further embodiment, the epilepsy is cryptogenic epilepsy. In another embodiment, the epilepsy is therapy resistant epilepsy; i.e. epilepsy that is unresponsive, partially responsive, incompletely responsive or poorly responsive to known methods for the treatment of epilepsy including but not limited to known anti-epilepsy drugs and all variants of ketogenic (i.e. high fat, low carbohydrate) diets.

In a further embodiment, the compounds of the application are useful in the treatment of all types of seizures and for suppressing seizure activity as manifested by physical symptoms and/or electrical activity of the brain as measured by EEG or other standard methods of measurement, in subjects, the seizures being of multiple origins of known or unknown aetiology leading to a diagnosis of epilepsy or another seizure disorder, for e.g. traumatic injury (such as due to accident, surgery, war, or deliberately induced and where trauma may be of recent or of distant origin and leading to seizures and a diagnosis of epilepsy or another seizure disorder), drug induced e.g. allergic reaction, drug reaction or poisoning including overdose, spontaneous or idiopathic where there is no known aetiology, due to developmental problems or a known genetic pre-disposition or seizures that are a consequence of a bacterial or viral illness e.g. meningitis.

Accordingly, the present application includes a method of treating seizures comprising administering one or more compounds of the application to a subject in need thereof. The present application also includes a use of one or more compounds of the application for treating seizures in a subject; a use of one or more compounds of the application for preparation of a medicament for treating seizures in a subject; and one or more compounds of the application for use to treat seizures in a subject. In an embodiment of the present application, the seizure is any seizure of known or unknown etiology leading to a diagnosis of epilepsy or another seizure disorder. In another embodiment, the seizure is induced by traumatic injury (e.g. due to accident, surgery, war or deliberately induced), drugs (e.g. an allergic reaction, a drug reaction or poisoning including overdose), developmental problems or a known genetic pre-disposition, a bacterial or viral infection (e.g. meningitis) or is spontaneous or idiopathic.

In an embodiment, the same mechanism which leads to anticonvulsant activity also produces beneficial cognitive effects. Compounds combining an anticonvulsant bonded to a moiety that leads to the metabolic production of ketones are therefore also useful to improve cognitive function and/or moderate cognitive decline in subjects such as humans and animals. In an embodiment, compounds of the application are used in the treatment of cognitive dysfunction in subjects, the cognitive dysfunction being of multiple origins of known or unknown aetiology e.g. cognitive decline with aging or due to traumatic injury, drug reaction, genetic pre-disposition, illness of bacterial, viral or genetic origin or cognitive decline as a consequence of disorders such as Parkinson's disease, Alzheimer's disease and other dementias and neurological deficits as defined in subjects such as humans and animals.

Accordingly, the present application includes a method of treating cognitive dysfunction comprising administering one or more compounds of the application to a subject in need thereof. The present application also includes a use of one or more compounds of the application for treating cognitive dysfunction in a subject; a use of one or more compounds of the application for preparation of a medicament for treating cognitive dysfunction in a subject; and one or more compounds of the application for use to treat cognitive dysfunction in a subject.

In an embodiment of the present application, the cognitive dysfunction is any cognitive dysfunction of known or unknown etiology. In another embodiment, the cognitive dysfunction is cognitive decline with aging or due to traumatic injury, drug reaction, genetic pre-disposition, illness of bacterial, viral or genetic origin or as a consequence of disorders such as Parkinson's disease, Alzheimer's disease and other dementias and neurological deficits.

The present application also includes a method of improving cognitive performance comprising administering one or more compounds of the application to a subject. The present application also includes a use of one or more compounds of the application for improving cognitive performance in a subject; a use of one or more compounds of the application for preparation of a medicament for improving cognitive performance in a subject; and one or more compounds of the application for use to improve cognitive performance in a subject. In an embodiment, the subject does not have cognitive dysfunction; i.e. the compound of the application is administered to enhance cognitive performance in a subject without cognitive dysfunction.

The present application also includes a method of treating anxiety comprising administering one or more compounds of the application to a subject in need thereof. The present application also includes a use of one or more compounds of the application for treating anxiety in a subject; a use of one or more compounds of the application for preparation of a medicament for treating anxiety in a subject; and one or more compounds of the application for use to treat anxiety in a subject. In an embodiment, the anxiety is related to cognitive decline. In another embodiment, the anxiety is unrelated to cognitive decline.

The present application also includes a method of treating chronic pain comprising administering one or more compounds of the application to a subject in need thereof. The present application also includes a use of one or more compounds of the application for treating chronic pain in a subject; a use of one or more compounds of the application for preparation of a medicament for treating chronic pain in a subject; and one or more compounds of the application for use to treat chronic pain in a subject.

In an embodiment, the subject is a mammal. In another embodiment, the subject is a human, a companion animal, or livestock. In a further embodiment, the subject is a human. It is an embodiment that the subject is a companion animal. In another embodiment, the companion animal is a dog, cat, rodent or rabbit. In a further embodiment, the subject is livestock. It is an embodiment that the livestock is cattle, sheep, pigs, goats or equines.

The one or more compounds of the application are used alone or, as noted above, in combination with other known agents useful for treating a disease, disorder or condition of the present application. For example, in an embodiment, the disease, disorder or condition of the present application is cognitive dysfunction and the one or more compounds of the application are used in combination with one or more other known agents useful for treating cognitive dysfunction. When used in combination with other known agents useful in treating a disease, disorder or condition of the present application, it is an embodiment that the one or more compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and include, for example, administering the two substances at the same time, within a few hours of each other, or administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of compounds of the application can vary depending on many factors such as the pharmacodynamic properties of the compound, the mode of administration, the age, health and weight of the recipient, the nature and extent of the symptoms of the disease, disorder or condition of the present application, the frequency of the treatment and the type of concurrent treatment, if any, and the clearance rate of the compound in the subject to be treated. One of skill in the art can determine the appropriate dosage based on the above factors. In an embodiment, the compounds of the application are administered initially in a suitable dosage that is optionally adjusted as required, depending on the clinical response. As a representative example, oral dosages of one or more compounds of the application will range between about 1 mg per day to about 1000 mg per day for a human adult or an animal. In an embodiment of the present application, the pharmaceutical compositions are formulated for oral administration and the compounds are, for example in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. In an embodiment, the compounds of the application are administered in a single daily dose or the total daily dose may be divided into two, three or four daily doses.

Assessing a compound of the application's activity for treating, for example, epilepsy can be done using any one or more of known assays. Examples of such assays include, but are not limited to, maximal electroshock seizure (MES) test, pentylenetetrazole (PTZ) test, amygdala kindling assay, mouse corneal kindling assay, genetic absence epileptic (GAERS) rat assay and/or 6-Hz psychomotor seizure model. These assays and other strategies for identifying improved anti-epileptic drugs are performed, for example, as described in Löscher, W. et al. *Nature Reviews*, 12: 757-776 (2013) or as described in the examples for MES, PTZ, 6-Hz psychomotor seizure and mouse corneal kindling tests.

The following non-limiting examples are illustrative of the present application:

EXAMPLES

Example 1

Synthesis and Characterization of Compounds (a) Synthesis of
2-(1-(hexanamidomethyl)cyclohexyl)acetic acid
(compound 1)

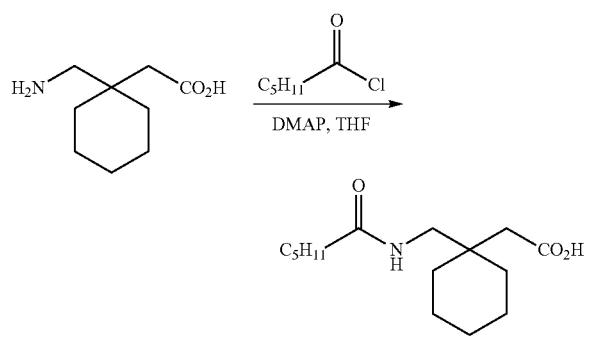

A suspension of 2-(1-(aminomethyl)cyclohexyl)acetic acid (2.0 g, 11.7 mmol) and 4-dimethylaminopyridine (DMAP; 1.43 g, 11.7 mmol) in anhydrous THF (40 mL) was treated with hexanoyl chloride (1.34 mL, 9.7 mmol) dropwise over a period of 5 min. at room temperature and stirred overnight (18 h). Solvent was removed under reduced pressure, crude was taken in $H_2O$ (200 mL) and acidified to pH ~1 with 6 N HCl. The crude product was extracted into EtOAc (2×150 mL). The combined organic layer was washed with brine (50 mL), dried ($Na_2SO_4$) and concentrated under reduced pressure to obtain the crude product. The crude was purified by column chromatography (EtOAc: Hexanes, 1:1) on silica gel to obtain the title compound 1 (1.4 g, 54%) as a white to off-white solid. $^1$H NMR (600 MHz, $CDCl_3$) δ 6.32 (s, 1H), 3.25 (d, J=6.6 Hz, 2H), 2.26-2.24 (m, 4H), 1.64-1.62 (m, 2H), 1.50-1.41 (m, 7H), 1.32-1.25 (m, 7H), 0.88-0.85 (m, 3H). ESI-MS (m/z, %): 268 (M-H, 100), 207 (50).

(b) Synthesis of
2-(1-(heptanamidomethyl)cyclohexyl)acetic acid
(compound 2)

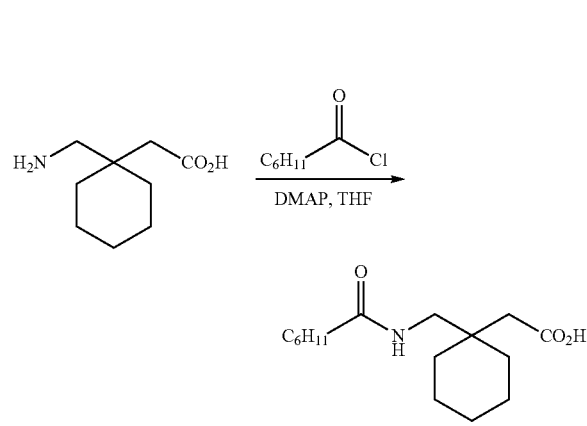

The title compound 2 was prepared from 2-(1-(aminomethyl)cyclohexyl)acetic acid (2.0 g, 11.7 mmol), DMAP (1.43 g, 11.7 mmol) and heptanoyl chloride (1.51 mL, 9.7 mmol) as described for compound 1. White to off-white solid (1.4 g, 51%). $^1$H NMR (600 MHz, $CDCl_3$) δ 6.45 (s, 1H), 3.25 (d, J=6.6 Hz, 2H), 2.26-2.24 (m, 4H), 1.63-1.61 (m, 2H), 1.50-1.41 (m, 7H), 1.31-1.26 (m, 9H), 0.855 (t, J=6.6 Hz, 3H). ESI-MS (m/z, %): 282 (M-H, 100).

(c) Synthesis of
2-(1-(octanamidomethyl)cyclohexyl)acetic acid
(compound 3)

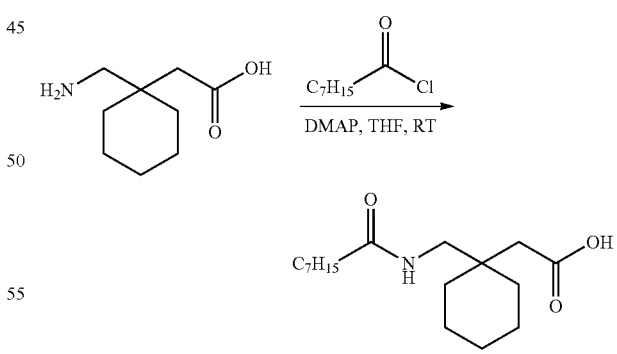

The title compound 3 was prepared from 2-(1-(aminomethyl)cyclohexyl)acetic acid (4.27 g, 24.9 mmol), DMAP (3.05 g, 24.9 mmol) and octanyl chloride (3.58 mL, 20.8 mmol) as described for compound 1. Pale yellow oil (2.2 g, 30%). $^1$H NMR (600 MHz, $CDCl_3$) δ 6.25 (s, 1H), 3.26-3.24 (m, 2H), 2.26-2.23 (m, 4H), 1.63-1.60 (m, 2H), 1.53-1.41 (m, 7H), 1.34-1.24 (m, 11H), 0.87-0.85 (m, 3H). ESI-MS (m/z, %): 296 (M-H, 100).

(d) Synthesis of 2-(1-(nonanamidomethyl)cyclohexyl)acetic acid (compound 4)

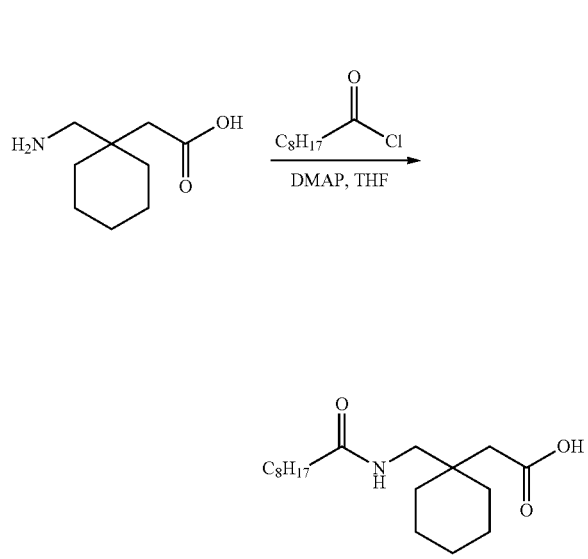

The title compound 4 was prepared from 2-(1-(aminomethyl)cyclohexyl)acetic acid (2.0 g, 11.7 mmol), DMAP (1.71 g, 14.0 mmol) and nonanoyl chloride (2.63 mL, 14.0 mmol) as described for compound 1. White solid (2.1 g, 58%). $^1$H NMR (600 MHz, CDCl$_3$) δ 6.40 (s, 1H), 3.25 (d, J=7.2 Hz, 2H), 2.26-2.24 (m, 4H), 1.63-1.61 (m, 2H), 1.50-1.41 (m, 7H), 1.29-1.23 (m, 13H), 0.85 (t, J=7.2 Hz, 3H). ESI-MS (m/z, %): 310 (M-H, 100).

(e) Synthesis of 2-(1-(decanamidomethyl)cyclohexyl)acetic acid (compound 5)

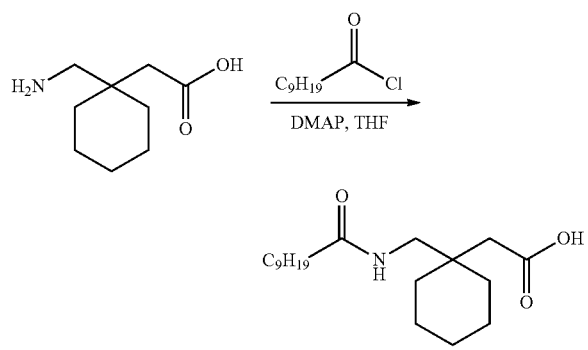

The title compound 5 was prepared from 2-(1-(aminomethyl)cyclohexyl)acetic acid (2.0 g, 11.7 mmol), DMAP (1.71 g, 14.0 mmol) and decanoyl chloride (2.89 mL, 14.0 mmol) as described for compound 1. White solid (1.7 g, 45%). $^1$H NMR (600 MHz, CDCl$_3$) δ 6.33 (s, 1H), 3.25 (d, J=6.6 Hz, 2H), 2.26-2.24 (m, 4H), 1.63-1.61 (m, 2H), 1.50-1.41 (m, 7H), 1.29-1.23 (m, 15H), 0.85 (t, J=7.2 Hz, 3H). ESI-MS (m/z, %): 324 (M-H, 100).

(f) Synthesis of 2-(1-(undecanamidomethyl)cyclohexyl)acetic acid (compound 6)

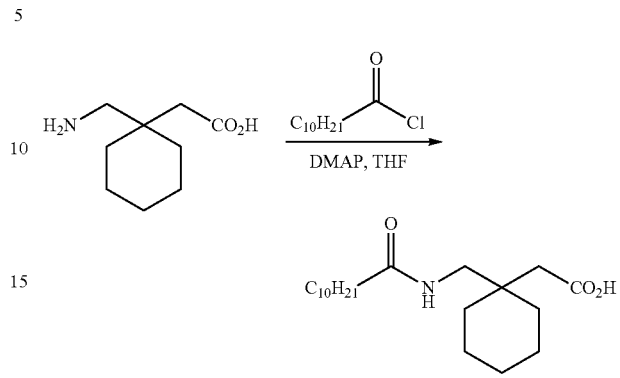

The title compound 6 was prepared from 2-(1-(aminomethyl)cyclohexyl)acetic acid (2.0 g, 11.7 mmol), DMAP (1.43 g, 11.7 mmol) and undecanoyl chloride (2.14 mL, 9.7 mmol) as described for compound 1. White to off-white solid (1.5 g, 45%). $^1$H NMR (600 MHz, CDCl$_3$) δ 6.31 (s, 1H), 3.25 (d, J=7.2 Hz, 2H), 2.26-2.24 (m, 4H), 1.63-1.61 (m, 2H), 1.53-1.41 (m, 7H), 1.29-1.23 (m, 17H) 0.85 (t, J=6.6 Hz, 3H). ESI-MS (m/z, %): 338 (M-H, 100).

(g) Synthesis of 2-(1-(dodecanamidomethyl)cyclohexyl)acetic acid (compound 7)

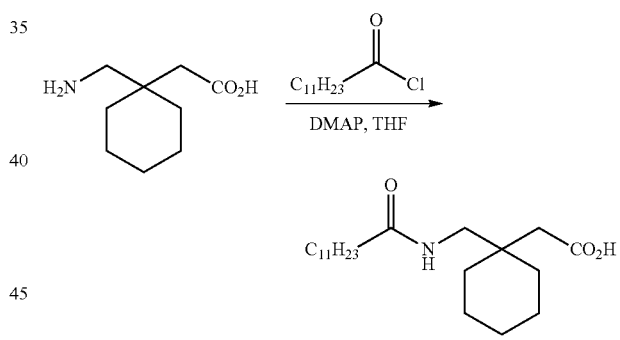

The title compound 7 was prepared from 2-(1-(aminomethyl)cyclohexyl)acetic acid (2.0 g, 11.7 mmol), DMAP (1.43 g, 11.7 mmol) and dodecanoyl chloride (2.31 mL, 9.7 mmol) as described for compound 1. White to off-white solid (1.8 g, 53%). $^1$H NMR (600 MHz, CDCl$_3$) δ 6.43 (s, 1H), 3.25 (d, J=6.6 Hz, 2H), 2.26-2.24 (m, 4H), 1.63-1.59 (m, 2H), 1.50-1.39 (m, 7H), 1.30-1.23 (m, 19H), 0.85 (t, J=7.2 Hz, 3H). ESI-MS (m/z, %): 352 (M-H, 100).

(h) Synthesis of 2-(1-((4-methyloctanamido)methyl)cyclohexyl)acetic acid (compound 8)

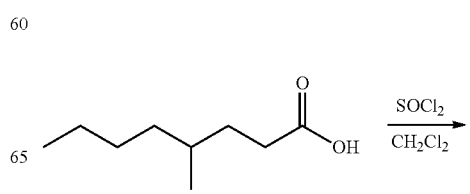

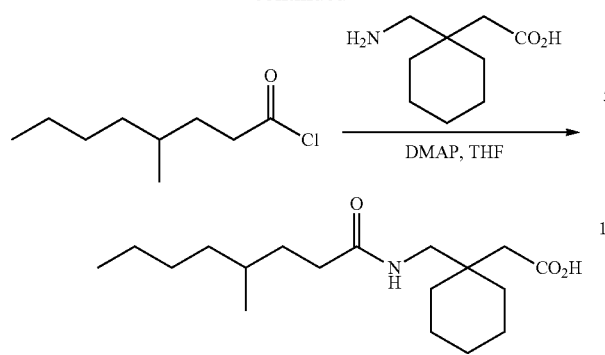

A solution of 4-methyl octanoic acid (1.5 g, 9.47 mmol) in CH$_2$Cl$_2$ (15 mL) was treated with SOCl$_2$ (2.07 mL, 28.4 mmol) drop-wise over a period of 5 min. at room temperature. The reaction was then heated to reflux for 3 h. The reaction was cooled to room temperature, then solvent and excess SOCl$_2$ were removed under reduced pressure to obtain the crude 4-methyl octanoyl chloride as a pale yellow oil. The title compound 8 was prepared from 2-(1-(aminomethyl)cyclohexyl)acetic acid (2.6 g, 15.1 mmol), DMAP (1.8 g, 15.1 mmol) and the above crude 4-methyl octanoyl chloride as described for compound 1. Colourless oil (1.4 g, 35%). $^1$H NMR (600 MHz, CDCl$_3$) δ 6.23 (brs, 1H), 3.25 (d, J=6.6 Hz, 2H), 2.29-2.23 (m, 4H), 1.68-1.62 (m, 1H), 1.53-1.37 (m, 10H), 1.30-1.19 (m, 8H), 1.12-1.08 (m, 1H), 0.88-0.85 (m, 6H). ESI-MS (m/z, %): 310 (M-H, 100).

(i) Synthesis of 2-(1-((2-propylpentanamido)methyl) cyclohexyl)acetic acid (compound 9)

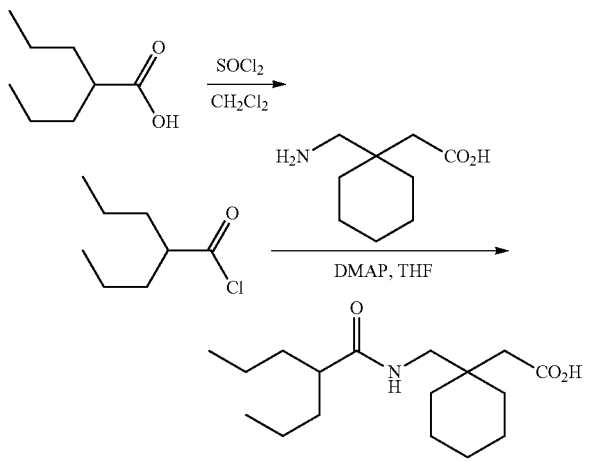

The title compound 9 was prepared from 2-propylpentanoic acid (5 g, 34.7 mmol; prepared as described for the 4-methyl octanoyl chloride used in the preparation of compound 8), 2-(1-(aminomethyl)cyclohexyl)acetic acid (7.1 g, 41.6 mmol) and DMAP (5.08 g, 41.6 mmol) as described for compound 1. White to off-white solid (3 g, 29%). $^1$H NMR (600 MHz, CDCl$_3$) 6.35 (s, 1H), 3.26 (d, J=6 Hz, 2H), 2.26 (s, 2H), 2.18-2.12 (m, 1H), 1.62-1.23 (m, 18H), 0.91-0.89 (m, 6H). ESI-MS (m/z, %): 296 (M-H, 100).

(j) Synthesis of (S)-3-(hexanamidomethyl)-5-methylhexanoic acid (compound 10)

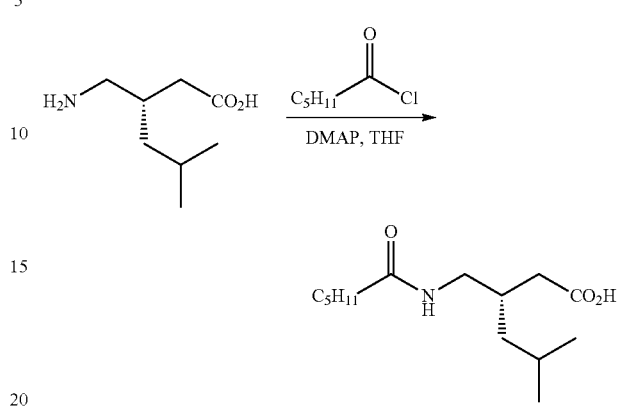

The title compound 10 was prepared from (S)-3-(aminomethyl)-5-methylhexanoic acid (2.0 g, 12.6 mmol), DMAP (1.50 g, 12.6 mmol) and hexanoyl chloride (1.40 mL, 10.5 mmol) as described for compound 1. Colourless oil (1.0 g, 40%). $^1$H NMR (600 MHz, CDCl$_3$) δ 6.08 (s, 1H), 3.36-3.31 (m, 1H), 3.20-3.15 (m, 1H), 2.33 (dd, J=4.2, 15 Hz, 1H), 2.24 (dd, J=7.8, 15 Hz, 1H), 2.19 (t, J=7.8 Hz, 2H), 2.09-2.04 (m, 1H), 1.70-1.59 (m, 3H), 1.30-1.23 (m, 4H), 1.18-1.16 (m, 2H), 0.89-0.85 (m, 9H). ESI-MS (m/z, %): 256 (M-H, 100).

(k) Synthesis of (S)-3-(heptanamidomethyl)-5-methylhexanoic acid (compound 11)

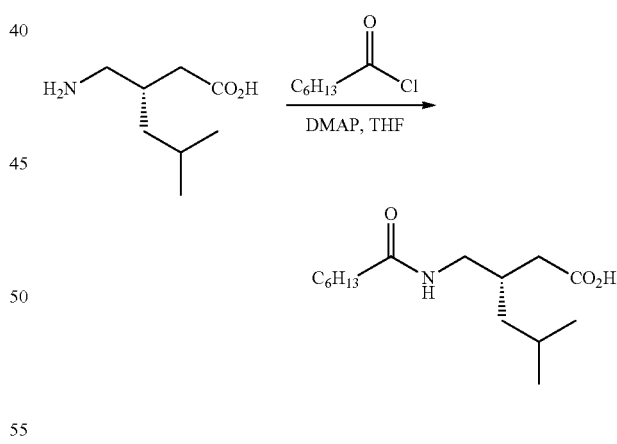

The title compound 11 was prepared from (S)-3-(aminomethyl)-5-methylhexanoic acid (2.0 g, 12.6 mmol), DMAP (1.50 g, 12.6 mmol) and heptanoyl chloride (1.60 mL, 10.5 mmol) as described for compound 1. Colourless oil (0.9 g, 32%). $^1$H NMR (600 MHz, CDCl$_3$) δ 6.07 (s, 1H), 3.36-3.32 (m, 1H), 3.20-3.16 (m, 1H), 2.32 (dd, J=4.8, 15 Hz, 1H), 2.24 (dd, J=8.4, 15 Hz, 1H), 2.19 (t, J=7.8 Hz, 2H), 2.10-0.04 (m, 1H), 1.70-1.59 (m, 3H), 1.30-1.23 (m, 6H), 1.18-1.16 (m, 2H), 0.89-0.84 (m, 9H). ESI-MS (m/z, %): 270 (M-H, 100).

(l) Synthesis of (S)-5-methyl-3-(octanamidomethyl)hexanoic acid (compound 12)

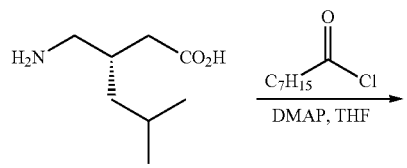

The title compound 12 was prepared from (S)-3-(aminomethyl)-5-methylhexanoic acid (2.65 g, 16.6 mmol), DMAP (2.03 g, 16.6 mmol) and octanoyl chloride (2.39 mL, 13.9 mmol) as described for compound 1. Pale yellow oil (0.9 g, 22%). $^1$H NMR (600 MHz, CDCl$_3$) δ 5.95 (brs, 1H), 3.39-3.35 (m, 1H), 3.23-3.19 (m, 1H), 2.35 (dd, J=4.2, 14.4 Hz, 1H), 2.28-2.20 (m, 3H), 2.11-2.05 (m, 1H), 1.70-1.62 (m, 3H), 1.31-1.16 (m, 10H), 0.92-0.87 (m, 9H). ESI-MS (m/z, %): 284 (M-H, 100).

(m) Synthesis of (S)-5-methyl-3-(nonanamidomethyl)hexanoic acid (compound 13)

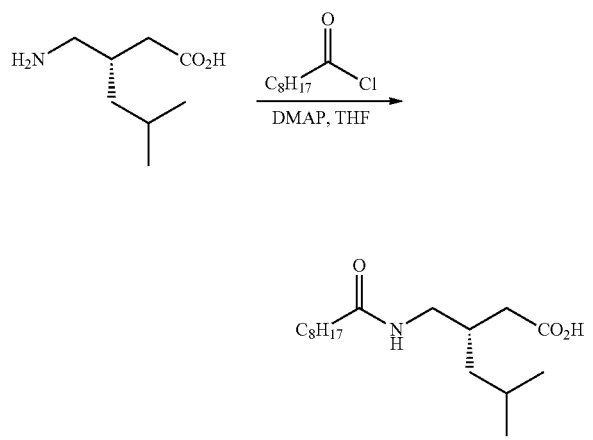

The title compound 13 was prepared from (S)-3-(aminomethyl)-5-methylhexanoic acid (2.0 g, 12.6 mmol), DMAP (1.84 g, 15.1 mmol) and nonanoyl chloride (2.83 mL, 15.1 mmol) as described for compound 1. Off-white solid (1.6 g, 42%). $^1$H NMR (600 MHz, CDCl$_3$) δ 5.95 (s, 1H), 3.37-3.33 (m, 1H), 3.21-3.16 (m, 1H), 2.32 (dd, J=4.8, 15 Hz, 1H), 2.24 (dd, J=7.8, 15 Hz, 1H), 2.19 (t, J=7.8 Hz, 2H), 2.08-2.02 (m, 1H), 1.67-1.59 (m, 3H), 1.28-1.12 (m, 12H), 0.89-81 (m, 9H). ESI-MS (m/z, %): 298 (M-H, 100).

(n) Synthesis of (S)-3-(decanamidomethyl)-5-methylhexanoic acid (compound 14)

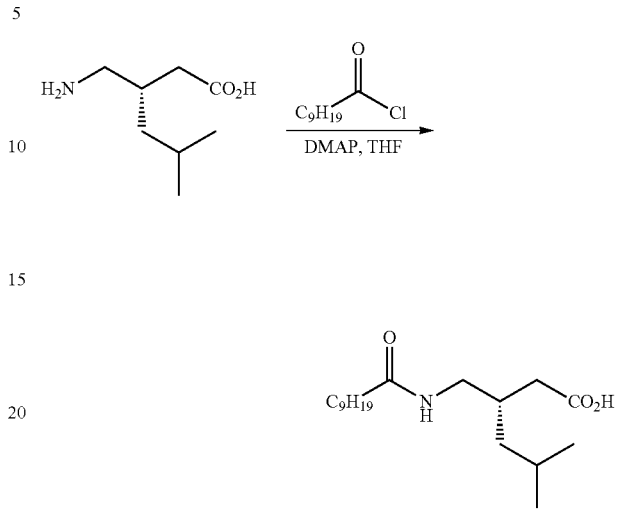

The title compound 14 was prepared from (S)-3-(aminomethyl)-5-methylhexanoic acid (2.0 g, 12.6 mmol), DMAP (1.84 g, 15.1 mmol) and decanoyl chloride (13.10 mL, 15.1 mmol) as described for compound 1. Off-white solid (2.0 g, 50%). $^1$H NMR (600 MHz, CDCl$_3$) δ 5.96 (s, 1H), 3.36-3.33 (m, 1H), 3.19-3.17 (m, 1H), 2.33 (dd, J=4.8, 15 Hz, 1H), 2.24 (dd, J=7.8, 15 Hz, 1H), 2.19 (t, J=7.2 Hz, 2H), 2.09-2.02 (m, 1H), 1.70-1.59 (m, 3H), 1.27-1.22 (m, 14H), 0.90-0.81 (m, 9H). ESI-MS (m/z, %): 312 (M-H, 100).

(o) Synthesis of (S)-5-methyl-3-(undecanamidomethyl)hexanoic acid (compound 15)

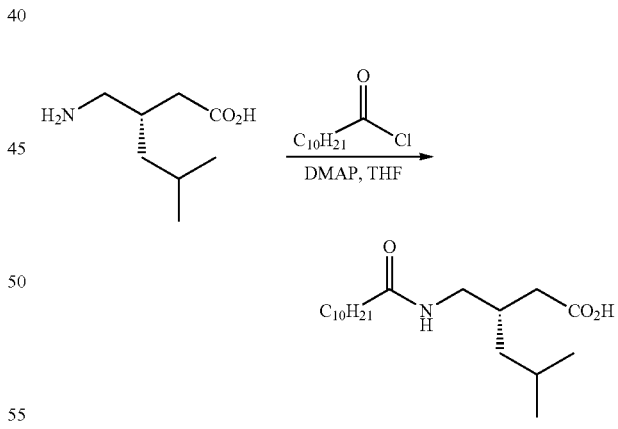

The title compound 15 was prepared from (S)-3-(aminomethyl)-5-methylhexanoic acid (2.0 g, 12.6 mmol), DMAP (1.5 g, 12.6 mmol) and undecanoyl chloride (2.3 mL, 10.5 mmol) as described for compound 1. Colourless oil (1.2 g, 35%). $^1$H NMR (600 MHz, CDCl$_3$) δ 6.02 (s, 1H), 3.36-3.32 (m, 1H), 3.20-3.15 (m, 1H), 2.32 (dd, J=4.2, 14.4 Hz, 1H), 2.24 (dd, J=7.8, 14.4 Hz, 1H), 2.19 (t, J=7.8 Hz, 2H), 2.10-2.04 (m, 1H), 1.70-1.59 (m, 3H), 1.30-1.22 (m, 14H), 1.18-1.16 (m, 2H), 0.89-0.84 (m, 9H). ESI-MS (m/z, %): 326 (M-H, 100).

(p) Synthesis of (S)-3-(dodecanamidomethyl)-5-methylhexanoic acid (compound 16)

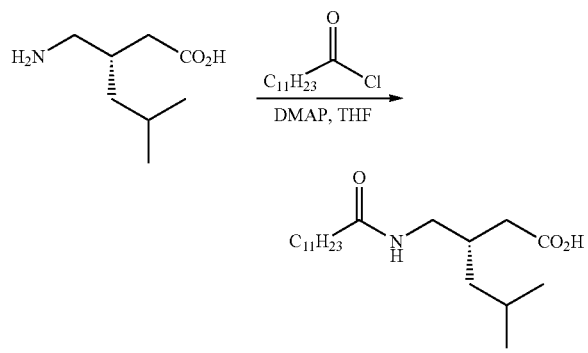

The title compound 16 was prepared from (S)-3-(aminomethyl)-5-methylhexanoic acid (2.0 g, 12.6 mmol), DMAP (1.50 g, 12.6 mmol) and dodecanoyl chloride (2.50 mL, 10.5 mmol) as described for compound 1. White solid (0.7 g, 19%). $^1$H NMR (600 MHz, CDCl$_3$) δ 6.02 (s, 1H), 3.35-3.32 (m, 1H), 3.20-3.17 (m, 1H), 2.32 (dd, J=10.2, 15 Hz, 1H), 2.24 (dd, J=7.8, 15 Hz, 1H), 2.18 (t, J=7.8 Hz, 2H), 2.10-2.04 (m, 1H), 1.70-1.58 (m, 3H), 1.27-1.23 (m, 16H), 1.18-1.16 (m, 2H), 0.89-0.84 (m, 9H). ESI-MS (m/z, %): 340 (M-H, 100).

(q) Synthesis of (S)-5-methyl-3-((2-propylpentanamido)methyl)hexanoic acid (compound 17)

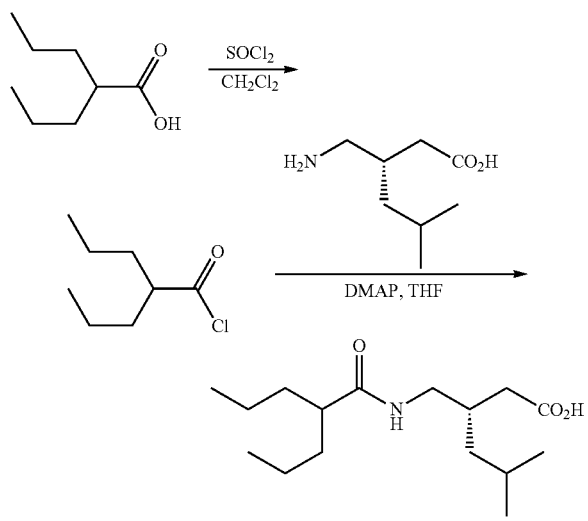

The title compound 17 was prepared from 2-propylpentanoic acid (2 g, 13.8 mmol; prepared as described for the 4-methyl octanoyl chloride used in the preparation of compound 8), (S)-3-(aminomethyl)-5-methylhexanoic acid (2.6 g, 16.6 mmol) and DMAP (2.0 g, 16.6 mmol) as described for compound 1. Pale yellow oil (1.1 g, 28%). $^1$H NMR (600 MHz, CDCl$_3$) 6.07 (s, 1H), 3.38-3.34 (m, 1H), 3.21-1.18 (m, 1H), 2.33 (dd, J=7.2, 15 Hz, 1H), 2.25 (dd, J=8.4, 15 Hz, 1H), 2.08-2.05 (m, 2H), 1.70-1.62 (m, 1H), 1.60-1.53 (m, 2H), 1.40-1.36 (m, 2H), 1.31-1.23 (m, 4H), 1.18-1.15 (m, 2H), 1.89-0.85 (m, 12H). ESI-MS (m/z, %): 284 (M-H, 100).

(r) Synthesis of (S)—N-(2-(2-oxopyrrolidin-1-yl)butanoyl)hexanamide (compound 18)

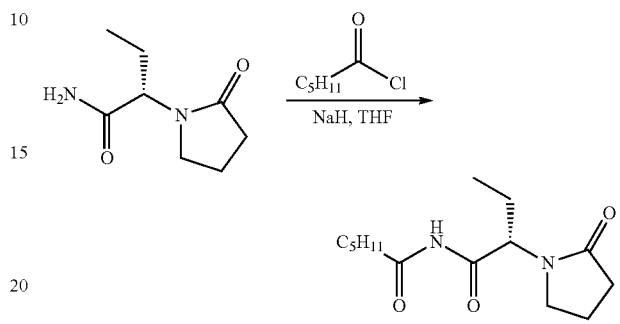

A suspension of (S)-2-(2-oxopyrrolidin-1-yl)butanamide (2 g, 11.7 mmol) in THF (30 mL) was treated with NaH (1.41 g, 35.2 mmol, 60% in mineral oil) portion-wise at 0° C. The reaction was allowed to warm to room temperature and stirred for a further 30 min. The reaction was treated with hexanoyl chloride (1.94 mL, 14.1 mmol) in THF (10 mL) drop-wise over a period of 5 min. at 0° C. The reaction was allowed to warm to room temperature and stirred overnight (16 h). The reaction was then quenched with H$_2$O (200 mL) and the product was extracted into EtOAc (2×150 mL). The combined organic layer was washed with brine (3×50 mL), dried (Na$_2$SO$_4$) and evaporated under reduced pressure to obtain the crude product. The crude was then purified by column chromatography (EtOAc: Hexanes, 1:1) on silica gel to obtain the title compound 18 (0.65 g, 21%) as a pale yellow oil. $^1$H NMR (600 MHz, CDCl$_3$) δ 8.85 (s, 1H), 4.55 (dd, J=3, 9 Hz, 1H), 3.42-3.38 (m, 2H), 2.63 (t, J=7.2 Hz, 2H), 2.46-2.42 (m, 2H), 2.07-2.03 (m, 2H), 1.97-1.93 (m, 1H), 1.71-1.59 (m, 3H), 1.30-1.28 (m, 4H), 0.91-0.85 (m, 6H). ESI-MS (m/z, %): 269 (MH$^+$, 100).

(s) Synthesis of (S)—N-(2-(2-oxopyrrolidin-1-yl)butanoyl)heptanamide (compound 19)

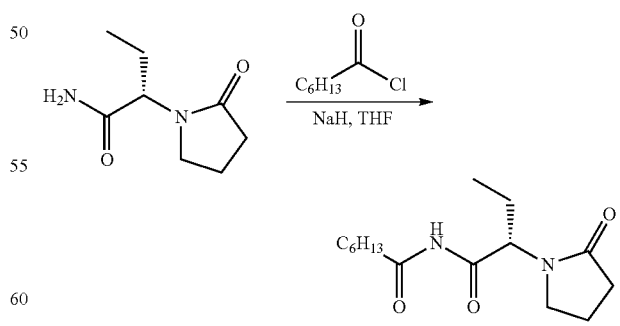

The title compound 19 was prepared from (S)-2-(2-oxopyrrolidin-1-yl)butanamide (2 g, 11.7 mmol) in THF (30 mL), NaH (1.41 g, 35.2 mmol, 60% in mineral oil) and heptanoyl chloride (2.18 mL, 14.1 mmol) as described for compound 18. Pale yellow oil (1.7 g, 51%). $^1$H NMR (600

MHz, CDCl$_3$) δ 8.75 (s, 1H), 4.53 (dd, J=2.4, 6.6 Hz, 1H), 3.41-3.38 (m, 2H), 2.64 (t, J=7.2 Hz, 2H), 2.46-2.42 (m, 2H), 2.06-2.02 (m, 2H), 1.99-1.92 (m, 1H), 1.73-1.58 (m, 3H), 1.33-1.23 (m, 6H), 0.92-0.85 (m, 6H). ESI-MS (m/z, %): 283 (MH$^+$, 100).

(t) Synthesis of (S)—N-(2-(2-oxopyrrolidin-1-yl)butanoyl)octanamide (compound 20)

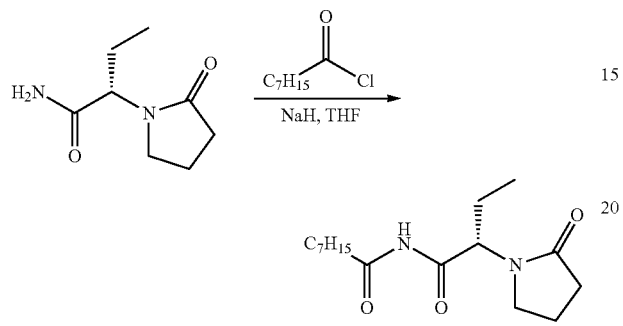

The title compound 20 was prepared from (S)-2-(2-oxopyrrolidin-1-yl)butanamide (2 g, 11.7 mmol), NaH (1.41 g, 35.2 mmol, 60% in mineral oil) and octanoyl chloride (2.43 mL, 14.1 mmol) as described for compound 18. Pale yellow oil (0.375 g, 37%). $^1$H NMR (600 MHz, CDCl$_3$) δ 8.76 (s, 1H), 4.54-4.51 (m, 1H), 3.41-3.38 (m, 2H), 2.64 (t, J=7.2 Hz, 2H), 2.46-2.42 (m, 2H), 2.07-1.95 (m, 3H), 1.71-1.56 (m, 3H), 1.30-1.22 (m, 8H), 0.90 (t, J=7.2 Hz, 3H), 0.85 (t, J=7.2 Hz, 3H). ESI-MS (m/z, %): 297 (MH$^+$, 100)

(u) Synthesis of (S)—N-(2-(2-oxopyrrolidin-1-yl)butanoyl)nonanamide (compound 21)

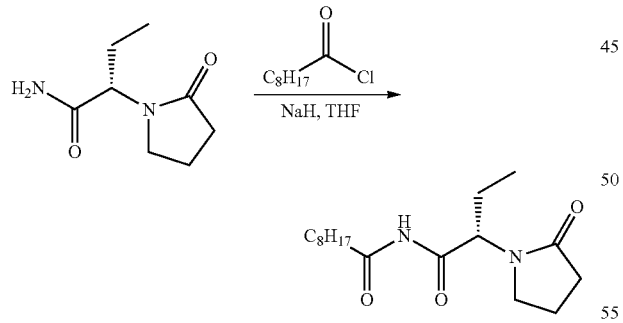

The title compound 21 was prepared from (S)-2-(2-oxopyrrolidin-1-yl)butanamide (2 g, 11.7 mmol), NaH (1.41 g, 35.2 mmol, 60% in mineral oil) and nonanoyl chloride (2.65 mL, 14.1 mmol) as described for compound 18. Pale yellow oil (2.163 g, 60%). $^1$H NMR (600 MHz, CDCl$_3$) δ 8.77 (s, 1H), 4.55-4.52 (m, 1H), 3.41-3.38 (m, 2H), 2.64 (t, J=7.2 Hz, 2H), 2.46-2.42 (m, 2H), 2.07-1.95 (m, 3H), 1.71-1.58 (m, 3H), 1.30-1.22 (m, 10H), 0.90 (t, J=7.2 Hz, 3H), 0.85 (t, J=7.2 Hz, 3H). ESI-MS (m/z, %): 311 (MH$^+$, 100).

(v) Synthesis of (S)—N-(2-(2-oxopyrrolidin-1-yl)butanoyl)decanamide (compound 22)

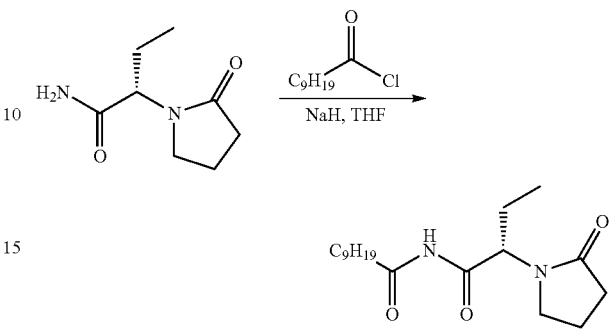

The title compound 22 was prepared from (S)-2-(2-oxopyrrolidin-1-yl)butanamide (2 g, 11.7 mmol), NaH (1.41 g, 35.2 mmol, 60% in mineral oil) and nonanoyl chloride (2.9 mL, 14.1 mmol) as described for compound 18. Pale yellow oil (1.98 g, 52%). $^1$H NMR (600 MHz, CDCl$_3$) δ 8.73 (s, 1H), 4.54-4.51 (m, 1H), 3.40-3.38 (m, 2H), 2.64 (t, J=7.2 Hz, 2H), 2.46-2.43 (m, 2H), 2.07-1.95 (m, 3H), 1.72-1.58 (m, 3H), 1.30-1.23 (m, 12H), 0.91 (t, J=7.2 Hz, 3H), 0.85 (t, J=7.2 Hz, 3H). ESI-MS (m/z, %): 325 (MH$^+$, 100).

(w) Synthesis of (S)—N-(2-(2-oxopyrrolidin-1-yl)butanoyl)undecanamide (compound 23)

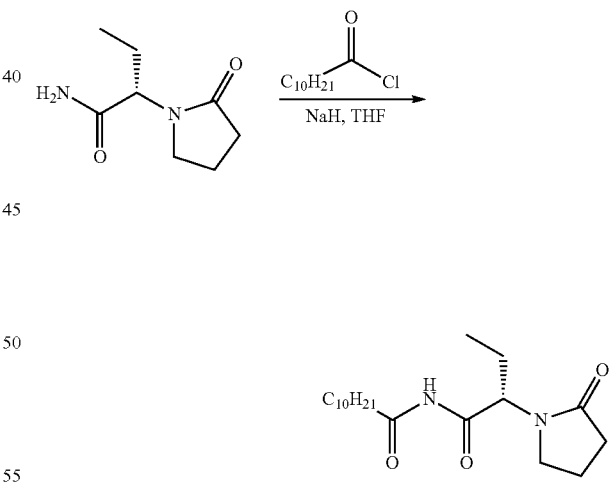

The title compound 23 was prepared from (S)-2-(2-oxopyrrolidin-1-yl)butanamide (2 g, 11.7 mmol), NaH (1.41 g, 35.2 mmol, 60% in mineral oil) and undecanoyl chloride (3.35 mL, 14.1 mmol) as described for compound 18. White to off-white solid (1.6 g, 39%). $^1$H NMR (600 MHz, CDCl$_3$) δ 8.72 (s, 1H), 4.52 (dd, J=3, 9 Hz, 1H), 3.39 (dt, J=1.2, 7.8 Hz, 2H), 2.64 (t, J=7.8 Hz, 2H), 2.46-2.43 (m, 2H), 2.09-2.02 (m, 2H), 1.99-1.93 (m, 1H), 1.72-1.68 (m, 1H), 1.62-1.58 (m, 2H), 1.30-1.22 (m, 14H), 0.92-0.89 (m, 3H), 0.88-0.85 (m, 3H). ESI-MS (m/z, %): 338 (MH$^+$, 100).

(x) Synthesis of (S)—N-(2-(2-oxopyrrolidin-1-yl)butanoyl)dodecanamide (compound 24)

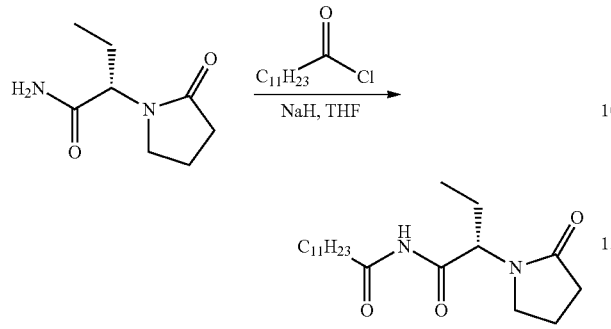

The title compound 24 was prepared from (S)-2-(2-oxopyrrolidin-1-yl)butanamide (2 g, 11.7 mmol), NaH (1.41 g, 35.2 mmol, 60% mineral oil) and dodecanoyl chloride (3.10 mL, 14.1 mmol) as described for compound 18. White to off-white solid (1.6 g, 40%). $^1$H NMR (600 MHz, CDCl$_3$) δ 8.75 (s, 1H), 4.53 (dd, J=2.4, 9 Hz, 1H), 3.39 (m, 2H), 2.64 (t, J=7.2 Hz, 2H), 2.46-2.43 (m, 2H), 2.07-2.04 (m, 2H), 1.98-1.95 (m, 1H), 1.72-1.68 (m, 1H), 1.61-1.58 (m, 2H), 1.30-1.23 (m, 16H), 0.91 (t, J=7.8 Hz, 3H), 0.85 (t, J=7.2 Hz, 3H). ESI-MS (m/z, %): 353 (MH$^+$, 100).

(y) Synthesis of 4-ethyl-N—((S)-2-(2-oxopyrrolidin-1-yl)butanoyl)octanamide (compound 25)

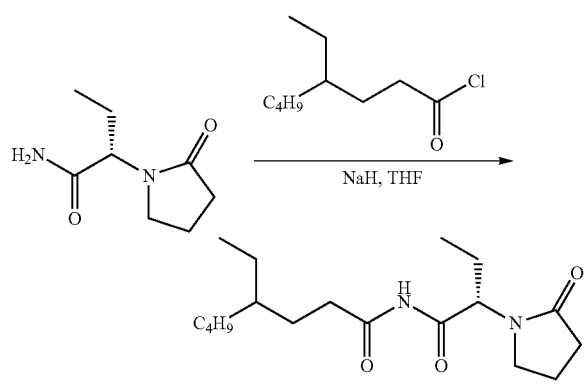

The title compound 25 was prepared from (S)-2-(2-oxopyrrolidin-1-yl)butanamide (3.56 g, 20.89 mmol), NaH (1.95 g, 51.08 mmol, 60% in mineral oil) and 4-ethyloctanoyl chloride (prepared from 4-ethyloctanoic acid (4.4 mL, 23.21 mmol) and thionyl chloride (5.0 mL, 69.65 mmol) as described for compound 8) as described for compound 18. Pale yellow oil (4.9 g, 72%). $^1$H NMR (600 MHz, CDCl$_3$) δ 8.67 (s, 1H), 4.51 (dd, J=2.4, 6.6 Hz, 1H), 3.38 (t, J=7.2 Hz, 2H), 2.64-2.61 (m, 2H), 2.46-2.43 (m, 2H), 2.07-2.05 (m, 2H), 2.02-1.95 (m, 1H), 1.75-1.65 (m, 1H), 1.57-1.55 (m, 2H), 1.28-1.20 (m, 9H), 0.90 (t, J=7.2 Hz, 3H), 0.86 (t, J=4.2 Hz, 3H), 0.82 (t, J=7.2 Hz, 3H); ESI-MS (m/z, %): 325 (MH$^+$, 100).

(z) Synthesis of (S)-4-butyl-N-(2-(2-oxopyrrolidin-1-yl)butanoyl)cyclohexane-1-carboxamide (compound 26)

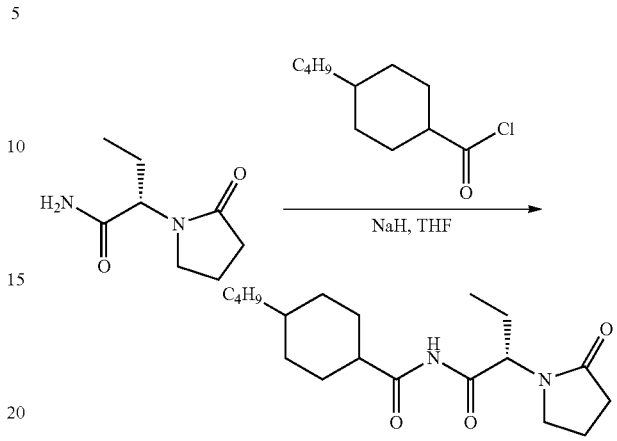

The title compound 26 was prepared from (S)-2-(2-oxopyrrolidin-1-yl)butanamide (3.13 g, 18.38 mmol), NaH (1.85 g, 48.46 mmol, 60% in mineral oil) and 4-butylcyclohexane-1-carbonyl chloride (prepared from 4-butylcyclohexane-1-carboxylic acid (3.5 g, 18.99 mmol) and thionyl chloride (4.1 mL, 56.69 mmol) as described for compound 8) as described for compound 18. White solid (3.95 g, 64%). $^1$H NMR (600 MHz, CDCl$_3$) δ 8.81 (s, 1H), 4.55 (dd, J=6.0, 9.0 Hz, 1H), 3.44-3.38 (m, 2H), 2.65-2.55 (m, 1H), 2.45-2.41 (m, 2H), 2.05-1.77 (m, 8H), 1.42-1.38 (m, 2H), 1.26-1.10 (m, 7H), 0.92-0.75 (m, 8H); ESI-MS (m/z, %): 337 (MH$^+$, 100).

Example 2

Efficacy in 6-Hz Psychomotor Seizure Model Predictive of Therapy-Resistant Epilepsy I. Materials and Methods Male, experimentally naive CD-1 mice were used in these experiments. At a defined time following drug or vehicle pretreatment, all mice received an electrical stimulus (6 Hz, 0.2 ms pulse width, 3 s duration, 32 mA) via corneal electrodes moistened with saline (ECT unit 57800; Ugo Basile). Preliminary experiments established that these stimulus parameters elicited a psychomotor seizure, defined as the expression of at least one of the following behaviors: stun/immobility, forelimb clonus, straub tail, lateral head movement, in >95% of control animals. Protection was defined as complete absence of all the above behaviors within 20 s of stimulus delivery. The effective dose of compound necessary to protect against psychomotor seizures to 50% of controls (i.e. ED$_{50}$) was determined by curve fitting program.

II. Results and Discussion

Figure 1:
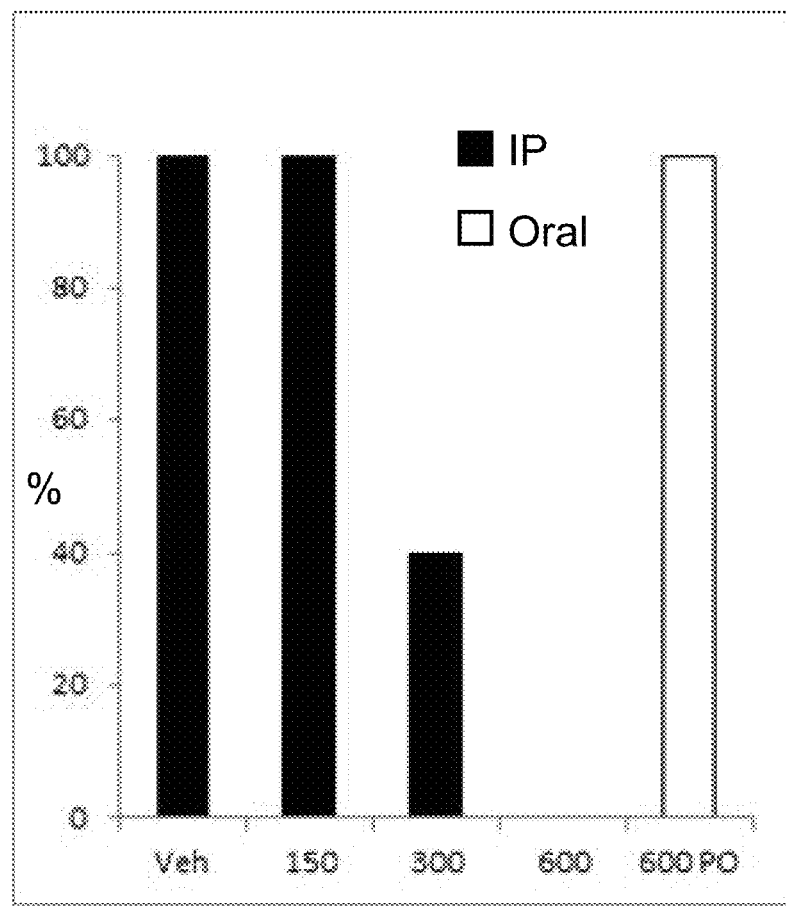
FIG. 1 is a plot showing the effect of increasing doses of compound 4 (150, 300 or 600 mg/kg IP; or 600 mg/kg oral; 1 h pretreatment) on the incidence of psychomotor seizures in CD-1 mice in comparison to a Vehicle ("Veh") control in an exemplary embodiment of the present application.

As can be seen in FIG. 1, pretreatment of compound 4 (150-600 mg/kg IP; 1 h pretreatment) produced a dose-related decrease in the incidence of seizures, such that all mice treated with compound 4 at 600 mg/kg IP were protected. In comparison, in mice treated with Vehicle (Veh), all mice had a seizure following 6-Hz stimulus. No mice were protected following oral pretreatment with compound 4 at 600 mg/kg.

Figure 2:
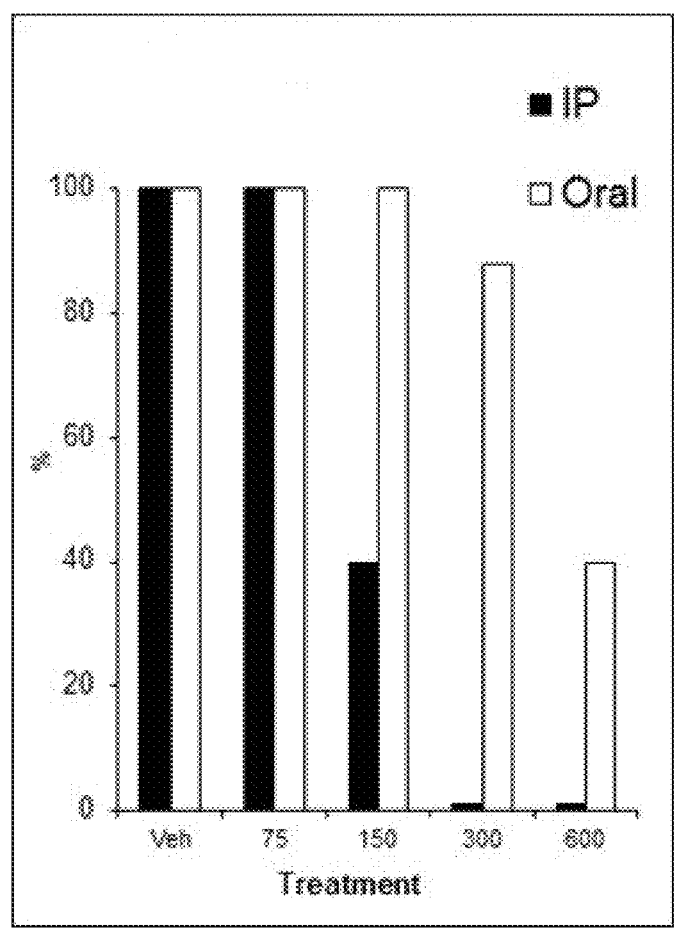
FIG. 2 is a plot showing the effect of increasing doses of compound 14 (75, 150, 300 or 600 mg/kg IP or oral; 1 h pretreatment) on the incidence of psychomotor seizures in CD-1 mice in comparison to a Vehicle ("Veh") control in an exemplary embodiment of the present application.

As can be seen in FIG. 2, pretreatment of compound 14 (75-600 mg/kg IP and oral routes; 1 h pretreatment) produced a dose-related decrease in the incidence of seizures, such that all mice treated with compound 14 at 300-600 mg/kg IP were protected. In comparison, in mice treated with Vehicle (Veh), all mice had a seizure following 6-Hz stimulus.

Figure 3:
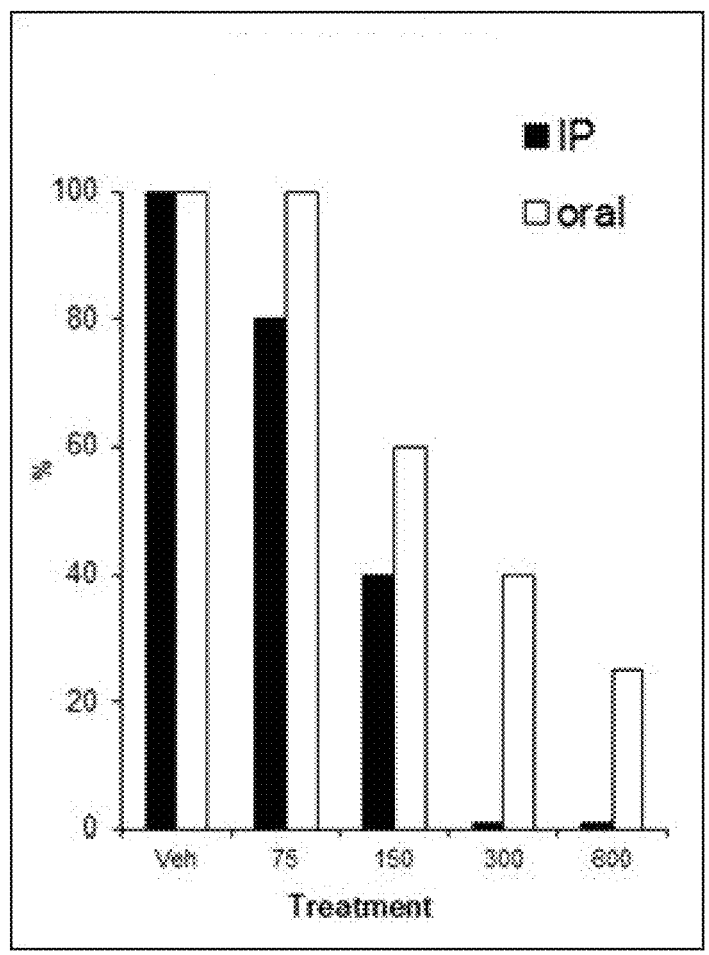
FIG. 3 is a plot showing the effect of increasing doses of compound 21 (75, 150, 300 or 600 mg/kg IP or oral; 1 h pretreatment) on the incidence of psychomotor seizures in CD-1 mice in comparison to a Vehicle ("Veh") control in an exemplary embodiment of the present application.

As can be seen in FIG. 3, pretreatment of compound 21 (75-600 mg/kg IP and oral routes; 1 h pretreatment) produced a dose-related decrease in the incidence of seizures, such that all mice treated with compound 21 at 300-600 mg/kg IP were protected. In comparison, in mice treated with Vehicle (Veh), all mice had a seizure following 6-Hz stimulus.

Figure 4:
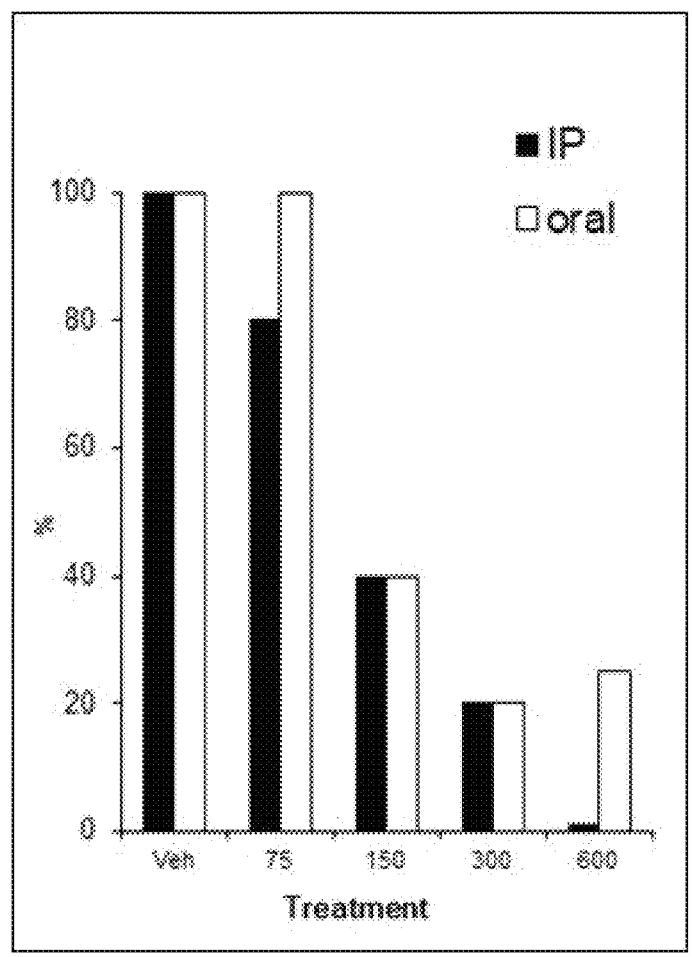
FIG. 4 is a plot showing the effect of increasing doses of compound 22 (75, 150, 300 or 600 mg/kg IP or oral; 1 h pretreatment) on the incidence of psychomotor seizures in CD-1 mice in comparison to a Vehicle ("Veh") control in an exemplary embodiment of the present application.

As can be seen in FIG. 4, pretreatment of compound 22 (75-600 mg/kg IP and oral routes; 1 h pretreatment) produced a dose-related decrease in the incidence of seizures, such that all mice treated with compound 22 at 600 mg/kg IP were protected. In comparison, in mice treated with Vehicle (Veh), all mice had a seizure following 6-Hz stimulus.

Figure 5:
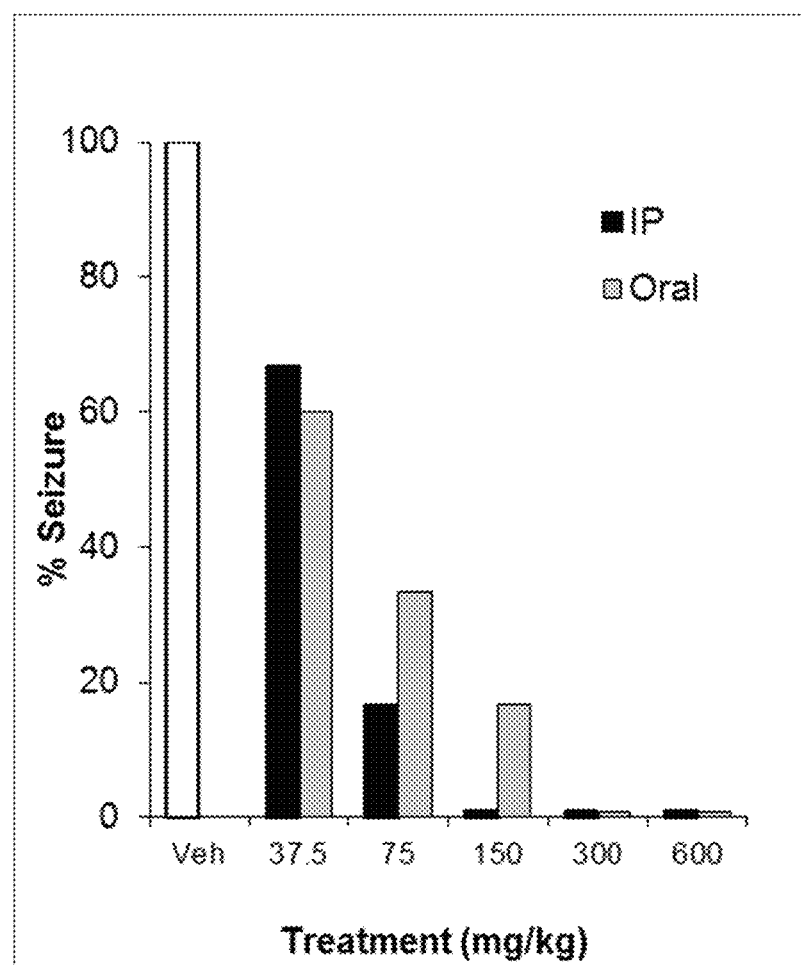
FIG. 5 is a plot showing the effect of increasing doses of compound 25 (37.5, 75, 150, 300 or 600 mg/kg IP or oral; 1 h pretreatment) on the incidence of psychomotor seizures in CD-1 mice in comparison to a Vehicle ("Veh") control in an exemplary embodiment of the present application.

As can be seen in FIG. 5, pretreatment of compound 25 (37.5-600 mg/kg IP and oral routes; 1 h pretreatment) produced a dose-related decrease in the incidence of seizures, such that all mice treated with compound 25 at 300 and 600 mg/kg IP were protected. In comparison, in mice treated with Vehicle (Veh), all mice had a seizure following 6-Hz stimulus.

Figure 6:
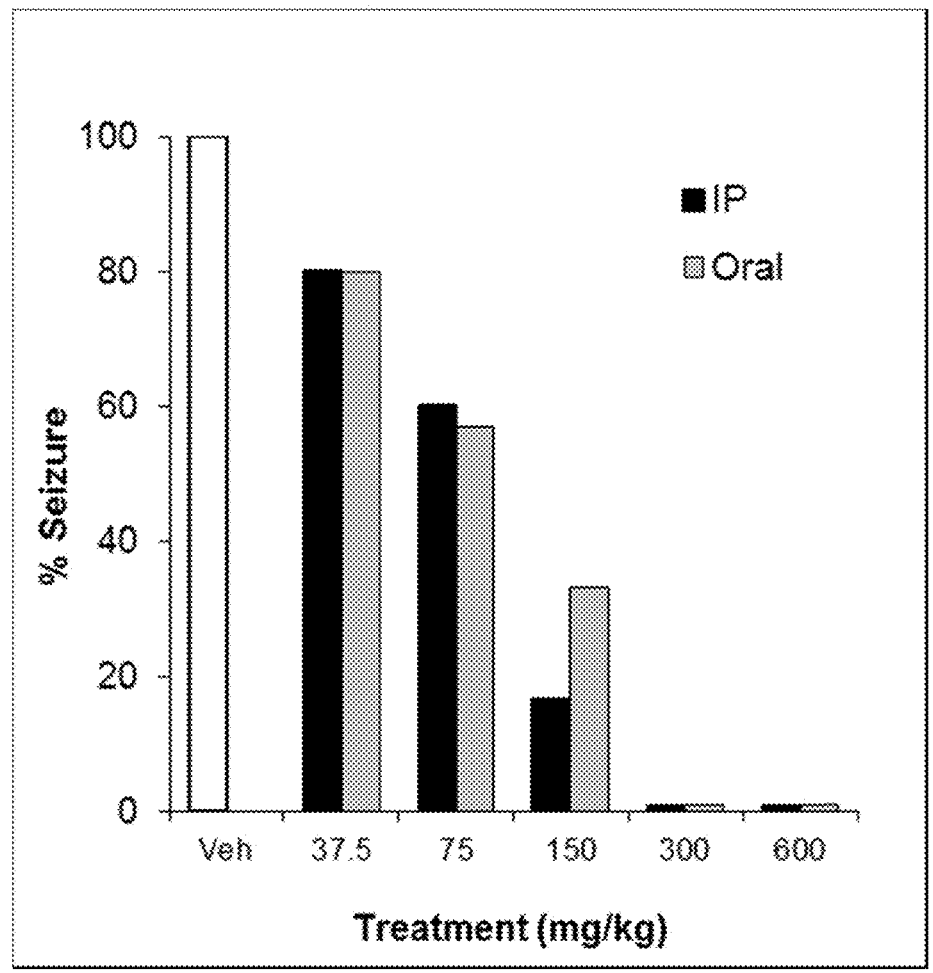
FIG. 6 is a plot showing the effect of increasing doses of compound 26 (37.5, 75, 150, 300 or 600 mg/kg IP or oral; 1 h pretreatment) on the incidence of psychomotor seizures in CD-1 mice in comparison to a Vehicle ("Veh") control in an exemplary embodiment of the present application.
Figure 7:
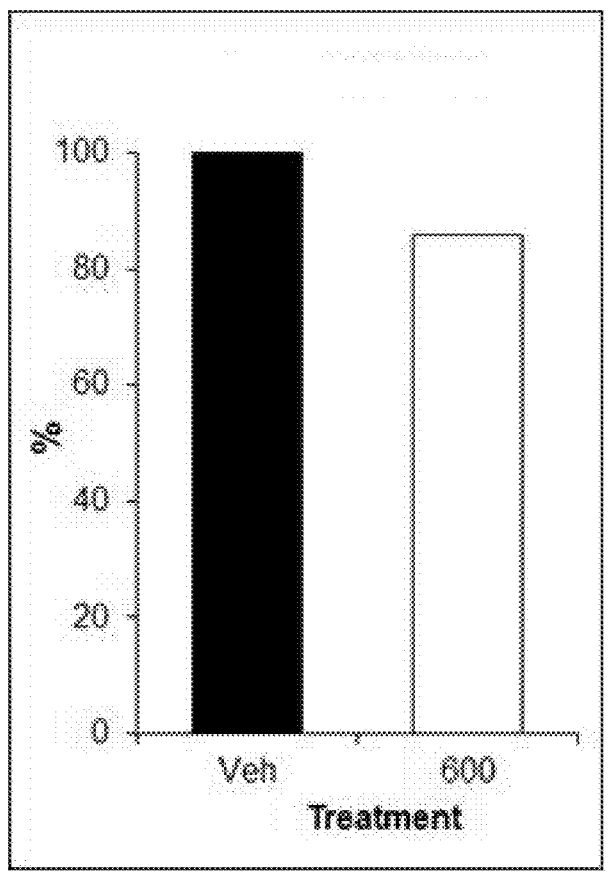
FIG. 7 is a plot showing the effect of compound 20 (600 mg/kg IP) in comparison to a Vehicle ("Veh") control against MES-induced tonic seizures, the incidence of which are expressed on the vertical axis as a percentage of the total sample population tested in an exemplary embodiment of the present application.

As can be seen in FIG. 6, pretreatment of compound 26 (37.5-600 mg/kg IP and oral routes; 1 h pretreatment) produced a dose-related decrease in the incidence of seizures, such that all mice treated with compound 26 at 300 and 600 mg/kg IP were protected. In comparison, in mice treated with Vehicle (Veh), all mice had a seizure following 6-Hz stimulus.

Example 3

Effect of Compounds 20, 25 and 26 in Mouse Seizure Tests

I. Methods

Male mice (body wt. 20-40 g) were used for all studies. Mice were used in one of the following 4 seizure tests: maximal electroshock seizure (MES) test, subcutaneous injection of pentylenetetrazol (scPTZ) test, seizures induced by 6 Hz stimulation (6 Hz), and corneal kindled seizures. These tests were selected because no single test detects all known anti-epileptic drugs (AED's), but all currently known AED's are detected as active (i.e. prevent seizures) in at least one of these tests. Subjects were tested in one of the 4 seizure tests following a defined time after treatment with either test drug or vehicle control. Following administration of test drug or vehicle by either the oral, subcutaneous or intraperitoneal route, the animals were tested according to one of the methods outlined below (1-4). Typically the pretreatment time was 60 minutes although in some cases this varied from 30 min to 4 h. With the exception of the corneal kindling model, once the animal had entered into a seizure, or passed a predetermined timepoint to demonstrate protection from a seizure, the endpoint was reached and the animal was immediately euthanised.

1. Maximal Electroshock Test (MES Test):

Male CD-1 mice received a maximal electroshock (45 mA, 0.2 s duration, 60 Hz) via corneal electrodes moistened with saline (shock stimulator type 221; Harvard apparatus). This stimulus intensity should elicit a full tonic seizure in >95% of control animals. Protection is defined as absence of a full tonic seizure within 15 s of stimulus delivery. To establish drug efficacy, test drug or vehicle was administered at a defined timepoint prior to the MES test, to separate experimental groups. The experiment was terminated immediately once the endpoint was met.

2. s.c. Pentylenetetrazol Seizure Test (PTZ Test):

Male CD-1 mice received a single subcutaneous injection of pentylenetetrazol (PTZ: 85 mg/kg). This dose of PTZ should elicit a clonic seizure in >95% of control animals. Following PTZ injection, the animals were immediately transferred to single observation cages and observed continuously for 30 min. To establish drug efficacy, test drug or vehicle was administered at a defined timepoint prior to the PTZ administration, to separate experimental groups. The effect of treatment on subsequent seizure was noted. Protection is defined as complete absence of a clonic seizure, including a forelimb clonus, over the 30 min observation period. In the event of a seizure, the onset latency from PTZ injection was recorded. The experiment was terminated immediately once the endpoint was met, or in the case of protection, at the completion of the 30 min test period.

3. 6 Hz Psychomotor Seizure Test:

Male CD-1 mice received an electrical stimulus (6 Hz, 0.2 ms pulse width, 3 s duration, 32 mA) via corneal electrodes moistened with saline (ECT unit 57800; Ugo Basile). These stimulus parameters should elicit a psychomotor seizure, defined as the expression of at least one of the following behaviours: stun/immobility, forelimb clonus, straub tail, vibrissae tremor, lateral head movement, in >95% of control animals within 30 s of stimulus delivery. To establish drug efficacy, test drug or vehicle was administered at a defined timepoint prior to the 6 Hz test, to separate experimental groups. The effect of treatment on subsequent seizure was noted. Protection is defined as complete absence of all the above behaviours within 20 s of stimulus delivery. The experiment was terminated immediately once the endpoint was met.

4. Mouse Corneal Kindling:

Male CD-1 mice (body wt. 20-40 g) were used for these studies. There are 3 phases to the procedure: (1) kindling development phase, (2) kindling stability/persistence phase, and (3) drug testing phase.

1. Kindling Development Phase:

Male mice received a mild electroshock (mice: 3 mA, 3 s duration, 60 Hz) via corneal electrodes moistened with saline (shock stimulator type 221; Harvard apparatus). This stimulus intensity should not initially elicit seizures, rather a mild behavioural response, e.g. brief (<5 s) immobility, stare. Mice received 2 such stimulations per day separated by a minimum period of 4 h (i.e. an a.m. stimulation and a p.m. stimulation), and daily for up to 25 days. Over a period of approximately 15 days, the animals developed transient behavioural changes typified by brief motor seizures for approximately 30 s following stimulation. These progressive behavioural changes were rated according to a scale developed by Racine (1972), i.e.

0=no reaction or immobility
1=jaw clonus
2=myoclonic twitches in the forelimbs, sometimes associated with head nodding
3=clonic convulsions limited to the forelimbs
4=clonic convulsions in the forelimbs with rearing and falling
5=generalised clonic convulsions associated with immediate loss of balance During repeated corneal stimulation, mice exhibiting a stage 3, 4 or 5 were defined as responders. Based on published validation studies (Matagne et al, 1998; Rowley et al, 2010) these should emerge after 10-15 days. Once the animals demonstrate at least 4 consecutive stage 3-5 seizures they were considered to be kindled and progressed to phase 2. Animals which did not reach stage 3-5 seizures by 25 consecutive days were considered non-responders and were removed from the study and euthanized.

2. Kindling Stability/Persistence Phase:

Before drug testing, an assessment of the persistence and stability of the kindled state was performed. This was achieved by giving test subjects a minimum of 2 days (maximum 10 days) without stimulation before resuming the twice daily stimulation protocol as described. Mice which demonstrated 4 consecutive stage 3-5 seizures at this point were considered to have a persistent and stable kindled state and ready for drug testing in phase 3. Mice that did not demonstrate 4 consecutive stage 3-5 seizures by 10 sessions of this second phase were removed from the study and euthanized.

3. Drug Testing Phase:

Drug testing was conducted using a repeated measures design with mice receiving up to 4 doses of a test drug and control treatments in a counterbalanced sequence. Drug test days were run with a 2-3 day interval with no stimulations administered on the intervening days. On a drug test day, the a.m. stimulation was preceded by a vehicle injection, and the p.m. stimulation was preceded by a drug injection. For each stimulation, the kindling score was assessed according to the Racine (1972) rating scale. Test compound or vehicle was administered by either the oral, subcutaneous or intraperitoneal route. Typically the pretreatment time was 1 h.

II. Results and Discussion

FIGS. 7-10 show the results of testing compound 20 in the above-described seizure tests. As can be seen in FIGS. 7-10, pretreatment of mice with compound 20 reduced seizures in comparison to a vehicle control.

FIGS. 11-13 show the results of testing compound 25 in the above-described seizure tests. As can be seen in FIGS. 11-13, pretreatment of mice with compound 25 reduced seizures in comparison to a vehicle control.

FIGS. 14-16 show the results of testing compound 26 in the above-described seizure tests. As can be seen in FIGS. 14-16, pretreatment of mice with compound 26 reduced seizures in comparison to a vehicle control.

Table 1 shows the ED50 values for compounds 20, 25 and 26 in the above tests.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A compound of Formula I(a)

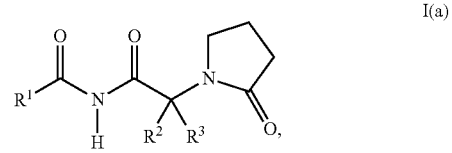

wherein:

$R^1$ is selected from $C_{4-15}$alkyl, $C_{4-11}$alkenyl, $C_{3-10}$cycloalkylene$C_{1-10}$alkyl, $C_{5-10}$cycloalkenylene$C_{1-10}$alkyl, $C_{3-10}$cycloalkylene$C_{2-10}$alkenyl and $C_{5-10}$cycloalkenylene$C_{2-10}$alkenyl; and $R^2$ and $R^3$ are each independently selected from H, $C_{1-8}$alkyl and $C_{2-8}$alkenyl; or $R^2$ and $R^3$ together with the carbon atom to which they are bonded form a $C_{3-10}$cycloalkane or a $C_{5-10}$cycloalkene, or a pharmaceutically acceptable salt, solvate and/or prodrug thereof.

2. The compound of claim 1, wherein $R^1$ is $C_{5-11}$alkyl, $C_{5-11}$alkenyl or cyclohexylene$C_{1-8}$alkyl.

3. The compound of claim 1, wherein $R^1$ is selected from n-pentyl, n-hexyl, n-heptyl, n-octyl, n-nonyl, n-decyl, n-undecyl, 3-methylheptyl, 1-propylbutyl, 3-ethylheptyl and 4-butylcyclohexyl.

4. The compound of claim 1, wherein $R^1$ is selected from n-heptyl, n-octyl, n-nonyl, 3-ethylheptyl and 4-butylcyclohexyl.

5. The compound of claim 1, wherein $R^2$ is H and $R^3$ is $C_{1-8}$alkyl or $C_{2-8}$alkenyl.

6. The compound of claim 1, wherein $R^2$ is H and $R^3$ is $C_{1-8}$alkyl.

7. The compound of claim 1, wherein $R^2$ is H and $R^3$ is $C_{1-4}$alkyl.

8. The compound of claim 1, wherein $R^2$ is H and $R^3$ is ethyl.

9. The compound of claim 1, wherein the compound is selected from:

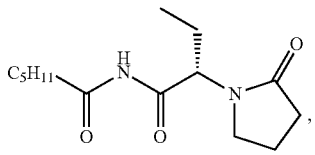

TABLE 1

| Mouse seizure models | Dose route | Compound 20 | | Compound 25 | | Compound 26 | |
|---|---|---|---|---|---|---|---|
| | | IP | PO | IP | PO | IP | PO |
| 6 Hz | EC50 (mg/kg) | 90 | 130 | 46 | 50 | 80 | 88 |
| | EC50 (mmol/kg) | 0.3 | 0.44 | 0.14 | 0.15 | 0.24 | 0.26 |
| MES | EC50 (mg/kg) | >600 | >600 | 397 | >600 | >600 | >600 |
| | EC50 (mmol/kg) | >2.02 | >2.02 | 1.22 | >1.85 | >1.78 | >1.78 |
| ScPTZ | EC50 (mg/kg) | >600 | >600 | 310 | 600 | 230 | 300 |
| | EC50 (mmol/kg) | >2.02 | >2.02 | 0.95 | 1.85 | 0.68 | 0.89 |

-continued

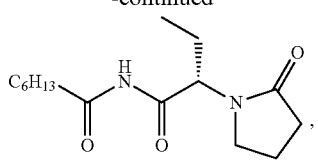

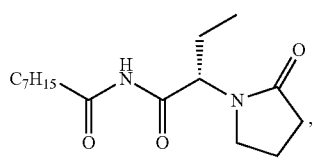

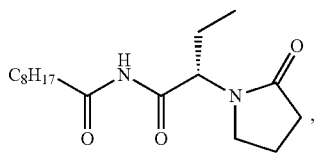

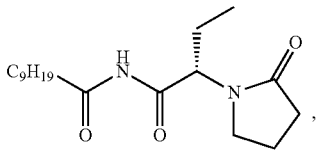

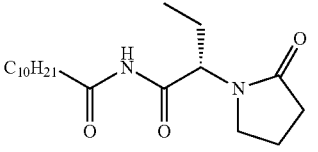

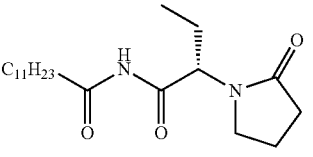

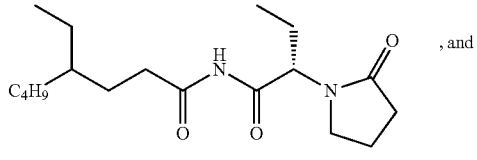, and

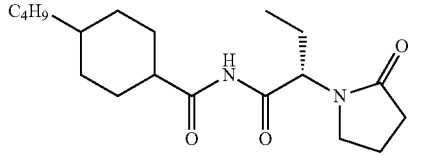, or a pharmaceutically acceptable salt, solvate and/or prodrug thereof.

10. The compound of claim 1, wherein the compound is:

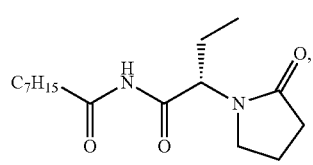

or a pharmaceutically acceptable salt, solvate and/or prodrug thereof.

11. The compound of claim 1, wherein the compound is:

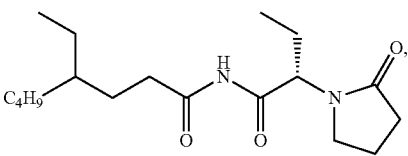

or a pharmaceutically acceptable salt, solvate and/or prodrug thereof.

12. The compound of claim 1, wherein the compound is:

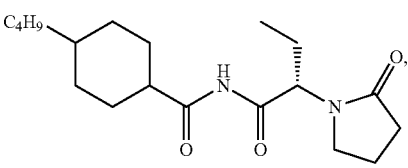

or a pharmaceutically acceptable salt, solvate and/or prodrug thereof.

13. The compound of claim 1, wherein the compound is selected from:

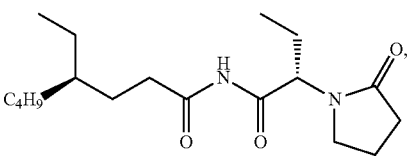

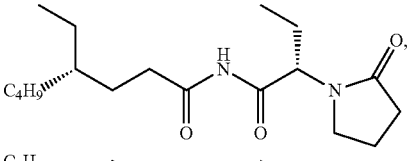

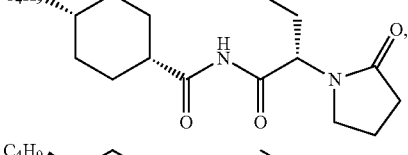

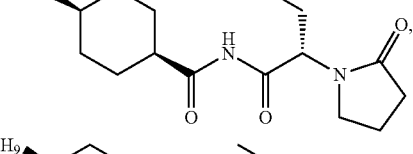, and

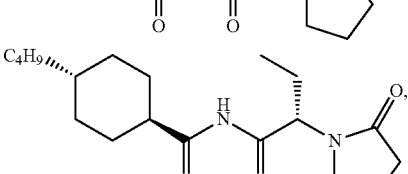, or a pharmaceutically acceptable salt, solvate and/or prodrug thereof.

14. A pharmaceutical composition comprising one or more compounds of claim 1, or a pharmaceutically acceptable salt, solvate and/or prodrug thereof, and a pharmaceutically acceptable carrier.

15. A method of treating a CNS disease, disorder or condition selected from epilepsy, non-epileptic seizures, cognitive dysfunction, cognitive performance, anxiety and chronic pain comprising administering one or more compounds of claim 1, or a pharmaceutically acceptable salt, solvate and/or prodrug thereof, to a subject in need thereof.

16. The method of claim 15, wherein the CNS disease, disorder or condition epilepsy.

17. A method of treating epilepsy comprising administering, to a subject in need thereof, one or more compounds of claim 1, or a pharmaceutically acceptable salt, solvate and/or prodrug thereof, in combination with an adjunct epilepsy treatment.

\* \* \* \* \*